United States Patent [19]

Krastinat

[11] 4,250,183
[45] Feb. 10, 1981

[54] N-(SUBSTITUTED AMINO)ALKANOYL-AMINOALKANOIC ACIDS AND SALTS, THEIR USE AND THEIR COMPOSITIONS

[75] Inventor: Walter Krastinat, Constance, Fed. Rep. of Germany

[73] Assignee: BYK Gulden Lomberg Chemische Fabrik GmbH, Constance, Fed. Rep. of Germany

[21] Appl. No.: 969,702

[22] Filed: Dec. 15, 1978

[30] Foreign Application Priority Data

Dec. 30, 1977 [LU] Luxembourg .......................... 78804

[51] Int. Cl.$^3$ .................. A61K 31/195; A61K 31/20; A61K 31/34; A61K 31/38
[52] U.S. Cl. ..................................... 424/263; 560/20; 560/49; 260/112.5 R; 560/117; 560/121; 260/326.2; 560/123; 560/124; 260/326.37; 560/125; 560/138; 260/326.47; 560/142; 562/426; 260/347.2; 562/427; 562/435; 260/347.3; 562/437; 562/448; 260/347.5; 562/449; 562/450; 260/402.5; 562/455; 562/456; 260/404.5; 562/457; 562/499; 260/463; 562/503; 562/505; 424/117; 562/506; 562/507; 424/266; 562/556; 562/557; 424/274; 562/561; 562/564; 424/275; 424/285; 424/301; 424/305; 424/308; 424/310; 424/311; 424/312; 424/314; 424/318; 424/319; 546/281; 546/316; 546/318; 546/323; 546/326; 549/71; 549/72; 560/18

[58] Field of Search ............... 562/426, 427, 435, 437, 562/455, 456, 457, 448, 449, 450, 499, 503, 505, 506, 507, 556, 557, 561, 564; 424/318, 319, 263, 266, 274, 275, 285, 177; 260/112.5 R, 402.5, 404.5, 326.2, 326.37, 326.47, 347.2, 347.3; 546/281, 316, 323; 549/72

[56] References Cited

U.S. PATENT DOCUMENTS

| | | | |
|---|---|---|---|
| 3,657,341 | 4/1972 | Thorne | 260/347.3 X |
| 4,000,139 | 12/1976 | Stutz et al. | 260/268 TR |
| 4,025,644 | 5/1977 | Miki et al. | 424/300 |
| 4,057,629 | 11/1977 | Miki et al. | 424/177 |
| 4,097,608 | 6/1978 | Miki et al. | 424/324 |
| 4,113,715 | 9/1978 | Ondetti et al. | 260/112.5 R |
| 4,129,571 | 12/1978 | Ondetti et al. | 260/326.2 |

OTHER PUBLICATIONS

Central Patent Index, Country Alerting Bulletin, Section B: Farmdoc Week A02 (1978), DT-B, p. 10, DT 2,727,670.

*Primary Examiner*—Richard Raymond
*Attorney, Agent, or Firm*—Berman, Aisenberg & Platt

[57] ABSTRACT

N-substituted ω-aminoalkanoyl-ω-aminoalkanoic acids and their pharmacologically-acceptable salts (with a base) are useful, e.g., in pharmaceutical-composition form for the treatment or prophylaxis of diseases which are based on inadequate performance of the pancreas, the bile and/or the liver. The compounds are prepared, e.g., by reacting an N-(mono- or di-substituted) ω-amino-alkanoic acid with an N-(unsubstituted or monosubstituted) ω-aminoalkanoic acid.

53 Claims, No Drawings

N-(SUBSTITUTED AMINO)ALKANOYL-AMINOALKANOIC ACIDS AND SALTS, THEIR USE AND THEIR COMPOSITIONS

BACKGROUND

N-acyl-ω-anilinoalkanoic acids produce a choleretic effect (U.S. Pat. No. 3,780,095), as well as other effects (U.S. Pat. No. 4,034,111). Trialkoxybenzoylpeptides (ZA 73 05 128 and DT-OS 2 338 172) are suitable for the prophylaxis and treatment of cardiac diseases. A new class of ω-aminoalkanoyl-ω-aminoalkanoic acids, which is neither mentioned in the cited published Patent Applications nor rendered obvious by them, has now been synthesized. These new compounds possess interesting and particularly advantageous pharmacological properties.

SUMMARY OF THE INVENTION

The compounds are acids of the formula

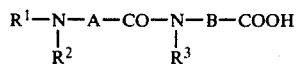   (I)

wherein $R^1$ is a carboxylic acid acyl (having up to 11 carbon atoms and up to one hetero atom of the group, oxygen, nitrogen and sulfur, in addition to carbonyl oxygen and contemplated substituents), e.g.

(1) hydrocarbyl-aliphatic carbonyl,
(2) hydrocarbyl-alicyclic carbonyl,
(3) benzoyl,
(4) substituted benzoyl,
(5) 2- or 3-furoyl,
(6) 2- or 3-thenoyl,
(7) nicotinoyl,
(8) isonicotinoyl,
(9) picolinoyl or
(10) 2- or 3-pyrrolecarbonyl;

$R^2$ is a hydrogen atom (—H), optionally-1-(hydrocarbyl-aliphatic)-substituted cycloalkyl with from 5 to 8 ring carbon atoms, adamantyl, substituted phenyl, branched-chain lower alkyl, substituted lower alkyl, or (when $R^3$ is other than straight-chain lower alkyl) straight-chain lower alkyl;

$R^3$ is straight-chain lower alkyl, branched-chain lower alkyl, substituted lower alkyl, phenyl, substituted phenyl, optionally-1-(hydrocarbyl-aliphatic)-substituted cycloalkyl with from 5 to 8 ring carbon atoms, adamantyl or [when $R^2$ is other than a hydrogen atom (—H)] a hydrogen atom (—H);

A is —(CH$_2$)$_m$— or —CH(R$^4$)—;
B is —(CH$_2$)$_n$— or —CH(R$^5$) —;

each of m and n is, independently, a positive whole number of at most 5;

each of $R^4$ and $R^5$ is, independently, methyl, benzyl, hydroxymethyl, 2-hydroxyethyl, methylmercaptomethyl or 2-methylmercaptoethyl;

or $R^3$ and $R^5$, together, are trimethylene; and salts of such acids with an inorganic or an organic base.

Compounds of formula I are prepared, e.g., by reacting an ω-aminoalkanoic acid of the formula

   (II)

with an ω-aminoalkanoic acid of the formula

   (III)

($R^1$, $R^2$, $R^3$, A and B having their previously-ascribed meanings).

The compounds are pharmacologically active and develop a stomach and liver protective action in warmblooded animals; in addition they bring about an increase in pancreas and liver (bile) secretion. The acids and those salts which are physiologically acceptable are advantageously incorporated in compositions of virtually all standard dosage forms for oral, rectal or parenteral administration. Such compositions are useful for the treatment and prophylaxis of diseases which are attributable to stomach or intestine disorders or to reduced performance of the pancreas, the gall bladder and/or the liver.

DETAILS

The invention particularly relates to N-[ω-(substituted amino)alkanoyl]-(ω-amino)alkanoic acids (Ia) of formula I in which $R^1$ signifies an aliphatic or alicyclic hydrocarbylcarbonyl radical, an optionally-substituted benzoyl group, a furoyl group, a thenoyl group or a nicotinoyl group, $R^2$ signifies a hydrogen atom (—H), a substituted lower alkyl radical or an optionally-substituted phenyl group, $R^3$ signifies a hydrogen atom (—H), an optionally-substituted lower alkyl radical or an optionally-substituted phenyl group (in which each of $R^2$ and $R^3$ does not simultaneously signify a hydrogen atom (—H) and each of $R^2$ and $R^3$ does not simultaneously signify a straight-chain lower alkyl radical), A signifies a —(CH$_2$)$_m$— group or a —CH(R$^4$)— group, B is a —(CH$_2$)$_n$— group or a —CH(R$^5$)— group, m and n are the same or different, each signifying a positive whole number from 1 to 5, $R^4$ and $R^5$ are the same or different, each being a methyl group, a benzyl group, a hydroxymethyl group, a 2-hydroxyethyl group, a methylmercaptomethyl group or a 2-methylmercaptoethyl group, or $R^3$ and $R^5$ together signify a trimethylene group, as well as their salts with an inorganic or organic base.

Aliphatic hydrocarbon radicals (hydrocarbyl) are either saturated or unsaturated, e.g. straight-chain or branched alkyl radicals with from 1 to 7 (preferably lower alkyl radicals with from 1 to 5) carbon atoms. Straight-chain alkyl radicals are methyl, ethyl, propyl, butyl, pentyl, hexyl or heptyl, of which those with from 1 to 5, especially with 1 or 2, carbon atoms are preferred. Branched alkyl radicals with from 3 to 7 carbon atoms are, for example, isopropyl, isobutyl, sec.-butyl or tert.-butyl, of which those with from 3 to 5, especially with 4, carbon atoms are preferred. Unsaturated hydrocarbyl radicals include alkenyl and alkynyl radicals with from 2 to 7 carbon atoms, e.g. ethenyl, 1-propenyl, ethinyl and propargyl, of which the 1-propenyl radical is preferred. Alicyclic hydrocarbon radicals (hydrocarbyl) are, e.g., cycloalkyl radicals with from 3 to 10 ring carbon atoms, such as cyclopropyl, cyclobutyl, cyclopentyl, cyclohexyl, cycloheptyl, cyclooctyl and adamantyl, of which those with from 6 to 10 carbon atoms are preferred.

Optionally-substituted benzoyl groups are advantageously those which have a phenyl group of the formula

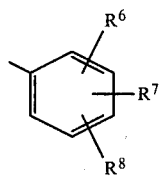 (Ph), in which $R^6$, $R^7$ and $R^8$ are the same or different, each signifying a hydrogen atom (—H), halo (e.g. fluoro, chloro, bromo, preferably fluoro and chloro, especially chloro), an alkyl group, a hydroxy group (—OH), an alkoxy group, an alkylmercapto group, an acyloxy group, an optionally-substituted amino group, a nitro group (—NO$_2$), a trifluoromethyl group (—CF$_3$), a trifluoromethoxy group (—OCF$_3$) or trifluoromethylmercapto (—SCF$_3$). As alkyl, alkoxy or alkylmercapto groups $R^6$, $R^7$ and $R^8$ primary interest is accorded those (straight-chain or branched) with from 1 to 4 carbon atoms, of which those with from 1 to 3, especially those with 1, carbon atom are preferred. The acyloxy groups are carboxylic acid or organic carbonic acid acyloxy groups, which include (but are not limited to) —O—$R^1$ groups, in which $R^1$ has its previously-ascribed meaning; alkanoyloxy groups with from 1 to 7, especially those with from 2 to 5, carbon atoms, particularly the acetoxy group, are preferred. Optionally-substituted amino includes unsubstituted amino (—NH$_2$) and substituted amino groups, e.g. alkylamino and dialkylamino groups with from 1 to 4, preferably 1 or 2, carbon atoms in each alkyl radical, as well as acylamino groups wherein the acyl is, e.g., $R^1$, particularly those with the usual acyl groups used for protecting amino groups, such as alkanoyl groups with from 2 to 5 carbon atoms.

Lower alkyl radicals $R^3$ are straight-chain or branched lower alkyl, such as those with from 1 to 5 carbon atoms, e.g. methyl, ethyl, isopropyl, isobutyl and n-butyl. Substituted lower alkyl radicals $R^2$ and/or $R^3$ are actually substituted methyl radicals of the formula —C($R^9$)($R^{10}$)($R^{11}$), in which $R^9$ signifies a hydrogen atom (—H), an alkyl group with from 1 to 5 carbon atoms, an alkenyl group with from 2 to 5 carbon atoms or an alkynyl group with from 2 to 5 carbon atoms, $R^{10}$ signifies a hydrogen atom (—H), an alkyl group with from 1 to 5 carbon atoms, a cycloalkyl group with 3 to 8 ring carbon atoms or an optionally-substituted phenyl radical (Ph), $R^{11}$ signifies an alkyl group with from 1 to 5 carbon atoms, a cycloalkyl group with from 3 to 8 ring carbon atoms, a cycloalkylalkyl group with 3 to 8 ring carbon atoms and from 1 to 3 carbon atoms in the alkyl group, a phenyl group (Ph) or a phenylalkyl group, (Ph)-alkyl, with from 1 to 3 carbon atoms in the alkyl group, or $R^{10}$ and $R^{11}$ together signify an alkylene group with from 4 to 7 carbon atoms or $R^9$, $R^{10}$ and $R^{11}$, with the inclusion of the carbon atom to which they are attached, signify an adamantyl radical, e.g. adamantyl-(1).

Unless otherwise specified all references to alkyl (including, but not limited to, "alkyl" of alkoxy, alkylmercapto, alkanoyl, alkanoyloxy, alkylamino, dialkylamino and phenylalkyl) are to either straight-chain (normal) or branched alkyl having at most 8 carbon atoms.

The preceding definition [—C($R^9$)($R^{10}$)($R^{11}$)] of substituted lower alkyl radicals $R^2$ and/or $R^3$ actually includes:

(i) straignt-chain or branched lower alkyl [$R^9$ is —H or alkyl; $R^{10}$ is —H or alkyl; and $R^{11}$ is alkyl];

(ii) substituted lower alkyl [$R^9$ is alkenyl or alkynyl; and/or $R^{10}$ is cycloalkyl or a phenyl group of formula Ph; and/or $R^{11}$ is cycloalkyl, cycloalkylalkyl, a phenyl group of formula Ph or a phenalkyl group, (Ph)-alkyl];

(iii) cycloalkyl [$R^9$ is —H; $R^{10}$ and $R^{11}$, together, are alkylene];

(iv) 1-substituted cycloalkyl [$R^9$ is alkyl, alkenyl or alkynyl; $R^{10}$ and $R^{11}$, together, are alkylene]; and (v) adamantyl [$R^9$, $R^{10}$ and $R^{11}$, together with the carbon atom to which they are bound, are 1-adamantyl].

Phenyl radicals and optionally-substituted phenyl correspond to previously-noted formula Ph.

The salts are salts of inorganic or organic bases. Pharmacologically-incompatible salts are converted by known methods into pharmacologically-, that is to say biologically-, compatible salts which are preferred. The principal cations for salt formation are cations of alkali metals, of alkaline-earth metals or of earth metals, but the corresponding cations of organic nitrogen bases, such as amines, aminoalkanols, amino sugars or basic amino acids, are also suitable for this purpose.

Exemplary salts are those of lithium, sodium, potassium, magnesium, calcium, aluminum, ethylenediamine, dimethylamine, diethylamine, morpholine, piperidine, piperazine, N-[lower alkyl-(e.g. methyl)]piperazines, methylcyclohexylamine, benzylamine, ethanolamine, diethanolamine, triethanolamine, tris-(hydroxymethyl)-aminomethane, 2-amino-2-methylpropanol, 2-amino-2-methyl-1,3-propandiol, glucamine, N-methylglucamine, glucosamine, N-methylglucosamine, lysine, ornithine, arginine and quinoline.

The invention further relates to compounds (Ib) which, in free-acid form, are of formula I, which includes each of the following formulae:

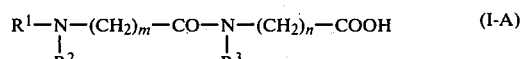 (I-A)

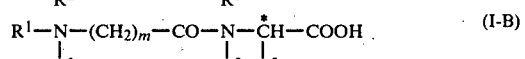 (I-B)

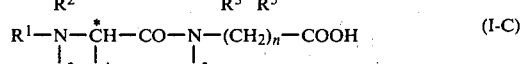 (I-C)

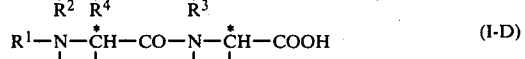 (I-D)

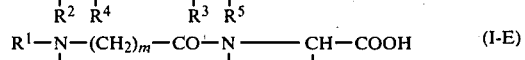 (I-E)

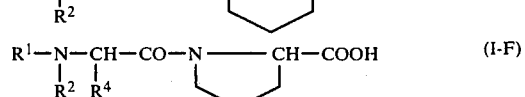 (I-F)

wherein $R^1$ is (1) hydrocarbyl aliphatic carbonyl, (2) hydrocarbyl alicyclic carbonyl, (3) benzoyl, (4) substituted benzoyl, (5) 2- or 3-furoyl, (6) 2- or 3-thenoyl, (7) nitotinoyl, (8) isonicotinoyl or (9) 2- or 3-pyrrolecarbonyl, particularly aliphatic carbonyl, alicyclic carbonyl, optionally-substituted benzoyl, 2-furoyl, 2-thenoyl or nicotinoyl;

$R^2$ is —H (but not when $R^3$ is —H), —C($R^9$)($R^{10}$)($R^{11}$), a phenyl group of the formula Ph, cycloalkyl with from 5 to 8 ring carbon atoms, 1-substituted cycloalkyl with from 5 to 8 ring carbon atoms or adamantyl;

$R^3$ is —H, methyl, —C($R^9$)($R^{10}$)($R^{11}$), a phenyl group of the formula Ph, cycloalkyl, 1-substituted cyclalkyl or adamantyl, with the proviso that $R^3$ is not lower alkyl when $R^2$ is lower alkyl;

$R^4$ is methyl, benzyl, hydroxymethyl, 2-hydroxyethyl, methylmercaptomethyl or 2-methylmercaptoethyl;

$R^5$ is, independently, one of the meanings ascribed to $R^4$;

each $R^9$ is, independently, —H, alkyl with from 1 to 5 carbon atoms, alkenyl with from 2 to 5 carbon atoms or alkynyl with from 2 to 5 carbon atoms;

each $R^{10}$ is, independently, —H, alkyl with from 1 to 5 carbon atoms, cycloalkyl with from 3 to 8 ring carbon atoms or a phenyl group of the formula Ph;

each $R^{11}$ is alkyl with from 1 to 5 carbon atoms, cycloalkyl with from 3 to 8 ring carbon atoms, cycloalkylalkyl with from 3 to 8 ring carbon atoms and from 1 to 3 carbon atoms in the alkyl, a phenyl group of the formula Ph or a phenalkyl group, (Ph)-alkyl with from 1 to 3 carbon atoms in the alkyl;

each of m and n is, independently, a positive whole number of at most 5; and * designates an asymmetric carbon atom.

The expression, "free-acid form", is directed to acids of each indicated formula and to all salts, preferably pharmacologically-acceptable salts, thereof with an inorganic or organic base.

A special group of compounds (Ic) of the invention is that which, in free-acid form, is of formula I and wherein $R^1$ signifies an alkanoyl radical with from 2 to 5 carbon atoms, an alkenoyl radical with from 2 to 5 carbon atoms, a furoyl radical or a benzoyl radical

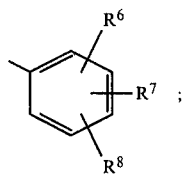

$R^2$ signifies a hydrogen atom (—H), —C($R^9$)($R^{10}$)($R^{11}$) or a phenyl group

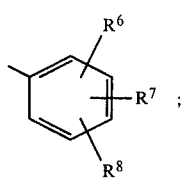

$R^3$ signifies a hydrogen atom (—H) or an optionally-substituted lower alkyl group, in which each of $R^2$ and $R^3$ does not simultaneously signify a hydrogen atom (—H), and each of $R^2$ and $R^3$ does not simultaneously represent a straight-chain lower alkyl group;

A signifies a —(CH$_2$)$_m$— group,

B signifies a —(CH$_2$)$_n$— group, m and n are the same or different, each signifying a positive integer from 1 to 5, each of $R^6$, $R^7$ and $R^8$ is, independently, a hydrogen atom (—H), halo, an alkyl group with from 1 to 4 carbon atoms, an alkoxy group with from 1 to 4 carbon atoms, an alkanoyloxy group with from 2 to 5 carbon atoms, amino, a hydroxy group (—OH), a nitro group or a trifluoromethyl group;

$R^9$ signifies a hydrogen atom (—H), an alkyl group with from 1 to 4 carbon atoms or an ethynyl group;

$R^{10}$ signifies a hydrogen atom (—H), an alkyl group with from 1 to 4 carbon atoms or a phenyl radical

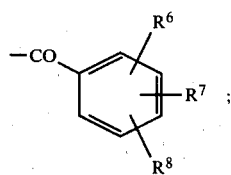

$R^{11}$ signifies an alkyl group with from 1 to 5 carbon atoms, a phenyl radical

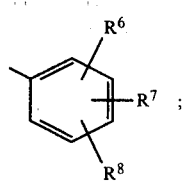

or a benzyl radical

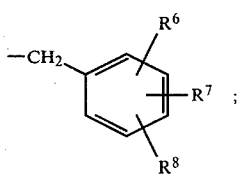

or $R^{10}$ and $R^{11}$, together, signify an alkylene group with from 4 to 7 carbon atoms;

or $R^9$, $R^{10}$ and $R^{11}$, with the inclusion of the neighboring carbon atom to which all three are bound, signify an adamantyl-(1) radical.

Preferred representatives of compounds Ic are those in which $R^1$ signifies an alkanoyl radical with from 2 to 5 carbon atoms or a benzoyl radical substituted with $R^6$, $R^7$ or $R^8$; $R^2$ signifies a hydrogen atom (—H), a group —C($R^9$)($R^{10}$)($R^{11}$) or a phenyl radical substituted with $R^6$, $R^7$ or $R^8$; $R^3$ signifies a hydrogen atom (—H), a group —C($R^9$)($R^{10}$)($R^{11}$) (in which $R^2$ and $R^3$ do not simultaneously signify a hydrogen atom, and $R^2$ and $R^3$ do not simultaneously represent a straight-chain lower alkyl group); A signifies a —(CH$_2$)$_m$— group; B signifies a —(CH$_2$)$_n$— group; m and n are the same or different and signify a positive whole number from 1 to 5; $R^6$ and $R^7$ are the same or different, each signifying a hydrogen atom (—H), a methyl group, a methoxy group, amino, halo, a nitro group or a trifluoromethyl group; $R^8$ signifies a hydrogen atom (—H), $R^9$ signifies a hydrogen atom (—H) or a methyl group; $R^{10}$ signifies a hydrogen atom (—H) or a phenyl radical substituted with $R^6$, $R^7$ or $R^8$ [or, together with $R^{11}$, represents a pentamethylene group or a heptamethylene group]; and $R^{11}$ signifies a phenyl radical substituted with $R^6$, $R^7$ or $R^8$ or a benzyl radical substituted with $R^6$, $R^7$ or $R^8$ or, jointly with $R^{10}$, represents a pentamethylene group or a heptamethylene group.

Particularly preferred representatives of compounds Ic are those in which $R^1$ signifies an alkanoyl radical with from 2 to 5 carbon atoms or a benzoyl radical substituted with $R^6$, $R^7$ or $R^8$; $R^2$ signifies a hydrogen atom (—H) or a phenyl group substituted with $R^6$, $R^7$ or $R^8$; $R^3$ signifies a hydrogen atom (—H) or a group $-C(R^9)(R^{10})(R^{11})$ (in which $R^2$ and $R^3$ do not simultaneously represent a hydrogen atom); A signifies a trimethylene group; B signifies a $-(CH_2)_n-$ group; n signifies a positive whole number from 3 to 5, $R^6$ signifies a hydrogen atom (—H), chloro, a methoxy group or a trifluoromethyl group; $R^7$ signifies a hydrogen atom (—H), chloro or a methoxy group, $R^8$ signifies a hydrogen atom (—H), $R^9$ signifies a hydrogen atom (—H); $R^{10}$ signifies a phenyl group substituted with $R^6$, $R^7$ or $R^8$; and $R^{11}$ signifies a phenyl group substituted with $R^6$, $R^7$ or $R^8$, a benzyl group substituted with $R^6$, $R^7$ or $R^8$.

Another group of compounds (Id) of the invention is that which, in free-acid form, is of formula I and wherein $R^1$ signifies an alkanoyl radical with from 2 to 5 carbon atoms, an alkenoyl radical with from 2 to 5 carbon atoms, a furoyl radical or a benzoyl radical

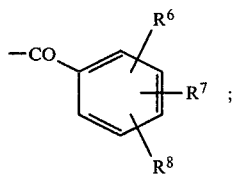

$R^2$ signifies a hydrogen atom (—H) or a phenyl group

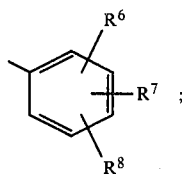

$R^3$ signifies a hydrogen atom (—H) or a phenyl group

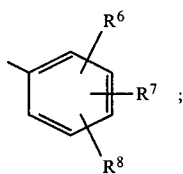

(in which $R^2$ and $R^3$ do not simultaneously represent a hydrogen atom);
A signifies a $-(CH_2)_m-$ group;
B signifies a $-(CH_2)_n-$ group;
m and n are the same or different, each signifying a positive whole number from 1 to 5; and
$R^6$, $R^7$ and $R^8$ are the same or different, each signifying a hydrogen atom (—H), halo, an alkyl group with from 1 to 4 carbon atoms, an alkoxy group with from 1 to 4 carbon atoms, an alkanoyloxy group with from 2 to 5 carbon atoms, amino, a hydroxy group (—OH), a nitro group or a trifluoromethyl group.

Preferred representatives of compounds Id are those in which $R^1$ signifies an alkanoyl radical with from 2 to 5 carbon atoms or a benzoyl radical substituted with $R^6$, $R^7$ or $R^8$; $R^2$ signifies a hydrogen atom (—H) or a phenyl radical substituted with $R^6$, $R^7$ or $R^8$; $R^3$ signifies a hydrogen atom (—H) or a phenyl radical substituted with $R^6$, $R^7$ or $R^8$ (in which $R^2$ and $R^3$ do not simultaneously represent a hydrogen atom); A signifies a $-(CH_2)_m-$ group; B signifies $-(CH_2)_n-$; m signifies a positive whole number from 1 to 3; n signifies a positive whole number from 3 to 5; $R^6$ signifies a hydrogen atom (—H); and $R^7$ and $R^8$ are the same or different, each signifying a hydrogen atom (—H), halo, a methyl group, an ethyl group, a methoxy group, amino, a nitro group or a trifluoromethyl group.

Particularly preferred representatives of compounds Id are those in which $R^1$ signifies an alkanoyl radical with from 2 to 5 carbon atoms or a benzoyl radical substituted with $R^6$, $R^7$ or $R^8$; $R^2$ signifies a phenyl radical substituted with $R^6$, $R^7$ or $R^8$; $R^3$ signifies a hydrogen atom (—H) or a phenyl radical substituted with $R^6$, $R^7$ or $R^8$; A signifies a $-(CH_2)_m-$ group; B signifies a trimethylene group; m signifies a positive whole number from 1 to 3; $R^6$ signifies a hydrogen atom (—H); $R^7$ signifies a hydrogen atom (—H), chloro, a methyl group, a methoxy group or a trifluoromethyl group; and $R^8$ signifies a hydrogen atom (—H), chloro, an ethyl group or a methoxy group.

A further group Ie of compounds of the invention is that which, in free-acid form, is of formula I and wherein $R^1$ signifies an alkanoyl radical with from 2 to 5 carbon atoms, an alkenoyl radical with from 2 to 5 carbon atoms, a furoyl radical or a benzoyl radical

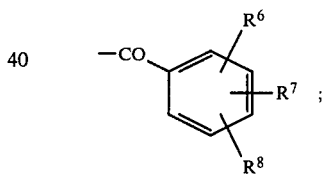

$R^2$ signifies a hydrogen atom (—H) or a phenyl radical

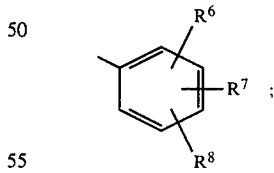

$R^3$ signifies a hydrogen atom (—H), a $-C(R^9)(R^{10})(R^{11})$ group or a phenyl group substituted with $R^6$, $R^7$ or $R^8$ or, together with $R^5$, a trimethylene group; and in which $R^2$ and $R^3$ do not simultaneously represent a hydrogen atom;
A signifies a $-(CH_2)_m-$ group or a $-CH(R^4)-$ group;
B signifies a $-(CH_2)_n-$ group or a $-CH(R^5)-$ group, and in which A and B do not simultaneously represent a straight-chain alkylene group;
m and n are the same or different, each signifying a positive whole number from 1 to 5;

$R^4$ signifies a methyl group, a benzyl group, a hydroxymethyl group or a 2-methylmercaptoethyl group;

$R^5$ signifies one of the meanings ascribed to $R^4$ or, together with $R^3$, a trimethylene group;

$R^6$, $R^7$ and $R^8$ are the same or different, each signifying a hydrogen atom (—H), halo, an alkyl group with from 1 to 4 carbon atoms, an alkoxy group with from 1 to 4 carbon atoms, an alkanoyloxy group with from 2 to 5 carbon atoms, amino, a hydroxy group (—OH), a nitro group or a trifluoromethyl group;

$R^9$ signifies a hydrogen atom (—H), an alkyl group with from 1 to 3 carbon atoms or an ethynyl group, $R^{10}$ signifies a hydrogen atom (—H), an alkyl group with from 1 to 3 carbon atoms, a cycloalkyl group with from 3 to 8 ring carbon atoms, a phenyl radical substituted with $R^6$, $R^7$ or $R^8$ or, together with $R^{11}$, an alkylene group with from 4 to 7 carbon atoms; and $R^{11}$ signifies an alkyl group with from 1 to 3 carbon atoms, a cycloalkyl group with 3 to 8 ring carbon atoms, a phenyl group substituted with $R^6$, $R^7$ or $R^8$, a benzyl group substituted with $R^6$, $R^7$ or $R^8$ or, together with $R^{10}$, an alkylene group with from 4 to 7 carbon atoms.

Preferred representatives of compounds Ie are those in which $R^1$ signifies an alkanoyl radical with from 2 to 5 carbon atoms or a benzoyl radical substituted with $R^6$, $R^7$ or $R^8$; $R^2$ signifies a hydrogen atom (—H) or a phenyl radical substituted with $R^6$, $R^7$ or $R^8$; $R^3$ signifies a phenyl radical substituted with $R^6$, $R^7$ or $R^8$ or, together with $R^5$, a trimethylene group; A signifies a —(CH$_2$)$_m$— or a —CH($R^4$)— group; B signifies a —(CH$_2$)$_n$— or a —CH($R^5$)— group [in which either A signifies a —(CH$_2$)$_m$— or B signifies a —(CH$_2$)$_n$— group, but not both concurrently]; m and n are the same or different, each signifying a positive whole number from 3 to 5; $R^4$ is a methyl group, a benzyl group, a hydroxymethyl group or a 2-methylmercaptoethyl group; $R^5$ is one of the meanings of $R^4$ or, together with $R^3$, a trimethylene group; $R^6$ signifies a hydrogen atom (—H), and $R^7$ and $R^8$ are the same or different, each signifying a hydrogen atom (—H), halo, a methyl group, a methoxy group, a nitro group, amino or a trifluoromethyl-group.

Particularly preferred representatives of compounds Ie are those in which $R^1$ signifies an alkanoyl radical with from 2 to 5 carbon atoms or a benzoyl radical substituted with $R^6$, $R^7$ or $R^8$; $R^2$ signifies a hydrogen atom (—H) or a phenyl radical substituted with $R^6$, $R^7$ or $R^8$; $R^3$ signifies a phenyl radical substituted with $R^6$, $R^7$ or $R^8$; A signifies a —CH($R^4$)— group; B signifies a trimethylene group; $R^4$ signifies a methyl group, a benzyl group or a 2-methylmercaptoethyl group; $R^6$ signifies a hydrogen atom (—H); $R^7$ signifies a hydrogen atom (—H), chloro, a methoxy group, a methyl group or a trifluoromethyl group; and $R^8$ signifies a hydrogen atom, chloro, a methyl group or a methoxy group.

Compounds Id and Ie are preferred, as compared with compounds Ic.

Illustrative of compounds of the invention are:

N-[N-(p-toluoyl)-4-(m-trifluoromethylanilino)butyryl]-4-(2,6-dimethylanilino)butyric acid, N-[N-(p-toluoyl)-3-(m-trifluoromethylanilino)propionyl]-4-(2,3-dimethylanilino)butyric acid, N-[N-(3,4-dimethylbenzoyl)-2-(m-trifluoromethylanilino)-propionyl-3-(2,6-dimethylanilino)propionic acid, N-[N-(p-toluoyl)-4-(o-anisidino)butyryl]-4-(p-anisidino)-butyric acid, N-[N-(3,4-dimethylbenzoyl)-3-(p-anisidino)propionyl]-4-(p-phenetidino)butyric acid, N-[N-(3,4-dimethoxybenzoyl)-4-(2,6-dimethylanilino)-butyryl]-4-(2,6-dimethylanilino)butyric acid, N-[N-(2-methoxy-5-chlorobenzoyl)-4-(p-anisidino)-butyryl]-4-(p-anisidino)butyric acid, N-[N-(2-methoxy-5-chlorobenzoyl)-3-(p-anisidino)propionyl]-3-(2,6-dimethylanilino)propionic acid, N-[N-(o-chlorobenzoyl)-4-(p-phenetidino)butyryl]-4-(2,6-dimethylanilino)butyric acid, N-[N-(o-chlorobenzoyl)-3-(2,6-dimethylanilino)propionyl]-4-(p-phenetidino)butyric acid, N-[N-(o-chlorobenzoyl)-3-(p-phenetidino)propionyl]-2-(p-phenetidino)propionic acid, N-[N-(p-fluorobenzoyl)-2-(2,6-dimethylanilino)acetyl]-4-(p-anisidino)butyric acid, N-[N-(o-fluorobenzoyl)-3-(2-chloro-4-methylanilino)-propionyl]-4-(2-chloro-4-methylanilino)butyric acid, N-[N-(3,5-dichlorobenzoyl)-3-(3,4-diethoxyanilino)propionyl]-2-(3,4-diethoxyanilino)propionic acid, N-[N-(p-acetamidobenzoyl)-4-(p-chloranilino)butyryl]-4-(2,4-dimethoxyanilino)butyric acid, N-[-(α, α, α-trifluoro-m-toluoyl)glycyl]-4-(2,6-dimethylanilino)butyric acid, N-[N-(2,4-dichlorobenzoyl)-α-alanyl]-4-(p-anisidino)-butyric acid, N-[N-p-nitrobenzoyl)-2-(o-toluidino)propionyl]-4-(o-toluidino)butyric acid, N-[N-(o-nitrobenzoyl)-3-(p-toluidino)propionyl]glycine, N-[N-(p-chlorobenzoyl)-4-(4-methyl-3-nitroanilino)-butyryl]-4-(3,4-dimethylanilino)butyric acid, N-[-N-benzoyl-(4-isopropylanilino)acetyl]-4-(4-methoxy-2-methylanilino)butyric acid, N-[N-(o-acetoxybenzoyl)-2-(p-anisidino)acetyl]-L-proline, N-[N-benzoyl-3-(3,4-dimethoxyanilino)propionyl]-L-proline, N-[N-(p-anisoyl)-2-(p-anisidino)acetyl]-L-proline, N-[N-(p-chlorobenzoyl)-4-(p-anisidino)butyryl]-4-benzhydrylaminobutyric acid, N-[N-(p-chlorobenzoyl)-3-(2,6-dimethylanilino)propionyl]-3-benzhydrylaminopropionic acid, N-[N-propionyl-4-(2,6-dimethylanilino)butyryl]-4-(2,6-dimethylanilino)butyric acid, N-[N-isobutyryl-3-(p-anisidino)propionyl]-4-(p-anisidino)-butyric acid, N-[N-crotonyl-4-(2,6-diethylanilino)butyryl]-4-(2,6-diethylanilino)butyric acid, N-[N-crotonoyl-α-alanyl)]-4-(2-chloro-6-methylanilino)butyric acid, N-[N-(p-chlorobenzoyl)-3-(p-anisidino)propionyl]-5-(p-anisidino)valeric acid, N-[N-(2-methoxy-5-chlorobenzoyl)-4-(2,6-dimethylanilino)-butyryl]-5-(2,6-dimethylanilino)valeric acid, N-[N-acetyl-4-(p-anisidino)butyryl]-6-benzhydrylaminohexanoic acid, N-[N-(2,4-dichlorobenzoyl)-6-(p-phenetidino)hexanoyl]-6-(p-phenetidino)hexanoic acid, N-[N-(p-chlorobenzoyl)-4-(p-anisidino)butyryl]-6-(2,6-dimethylanilino)hexanoic acid, and their salts with an inorganic or organic base.

As preferred embodiments of the invention are the following compounds and their pharmacologically-compatible salts with an inorganic or organic base:

N-[N-acetyl-2-(p-anisidino)acetyl]-4-(p-anisidino)-butyric acid,

N-[N-(p-chlorobenzoyl)-4-(2,6-dimethylanilino)-butyryl]-4-(p-anisidino)butyric acid, N-[N-(p-chlorobenzoyl)-4-(2,6-dimethylanilino)-butyryl]-4-aminobutyric acid, N-[N-(3,4,5-trimethoxybenzoyl)-4-(2,6-dimethylanilino)-butyryl]-4-aminobutyric acid, N-[N-acetyl-3-(2,6-dimethylanilino)propionyl]-4-(2-ethyl-6-methylanilino)butyric acid, and N-[N-(p-chlorobenzoyl)methionyl]-4-(p-anisidino)-butyric acid.

Compounds of the invention which contain one or more asymmetric carbon atoms (chirality centers), for example those in which a —CH($R^4$)— group, —CH($R^5$)— group and/or —C($R^9$)($R^{10}$)($R^{11}$) group (in which $R^9$, $R^{10}$ and $R^{11}$ are different) occur, are obtained from racemic initial materials in the form of racemates or of mixtures of diastereomers which are conventionally separated into respective enantiomers, for example, with the help of optically-active bases or on the basis of differences between their physicochemical properties. When optically-active compounds are used as initial materials, end products are obtained in optically-active form.

The compounds of the invention possess valuable pharmacological properties which make them commercially useful. In warm-blooded animals they develop a stomach and liver protective action; in addition they bring about an increase in pancreas and liver (bile) secretion.

Because of their advantageous pharmacological activity the N-substituted ω-aminoalkanoyl-ω-aminoalkanoic acids of this invention and their physiologically-acceptable salts with a base are suitable for treatment (alleviating and reducing symptons) and prophylaxis of diseases (which are attributable to stomach or intestine disorders or to reduced performance of the pancreas, the gall bladder and/or the liver), e.g. for treating gastric or intestinal ulcers, Billroth II, pancreatic insufficiency, sprue, indigestion and malabsorption of different aetiology, acute and chronic pancreatitis, indirect disturbances of the pancreatic function (supporting the secretin and pancreozymine production), as well as gall bladder and gall duct inflammation, disturbances in the flow of bile, motility disturbances of the gall ducts, a feeling or repletion, flatulence, constipation, upper abdominal complaint, hepato-biliary functional disorders, acute and chronic hepatitis, liver intoxication and fatty liver.

The invention comprises pharmaceutical compositions and other pharmaceutical products which contain one or more pharmacologically-acceptable compounds which, in free-acid form, are N-substituted ω-aminoalkanoyl-ωaminoalkanoic acids of formula I.

More-limited groups of corresponding pharmaceutical products contain compounds Ia, Ib, Ic, Id and/or Ie, including both N-substituted ω-aminoalkanoyl-ω-aminoalkanoic acids and their pharmacologically-compatible salts with an inorganic or organic base.

The pharmaceutical products are conventionally produced according to known processes. As pharmaceutical products the new compounds are useful as such or, if desired, in combination with suitable pharmaceutical carrier, excipient or other pharmacologically-inert additive. When the new pharmaceutical preparations, in addition to active principle, contain pharmaceutical carrier, excipient and/or other additive in admixture or other combination, the active principle content is from 1 to 95, preferably from 15 to 85, percent by weight of the total preparation.

In the field of human and veterinary medicine the active principles (physiologically-acceptable compounds which, in free-acid form, are compounds of formula I) are useful in any desired form, for example systemic, provided that the formation or maintenance of adequate blood or tissue levels or local concentrations of active principle is ensured. This is effected by oral, rectal or parenteral administration in suitable doses. More advantageously, the pharmaceutical preparation of active principle is in a unit-dose form, tailored to a particular type of contemplated administration. A unit dose is, for example, in the form of a tablet, a pill, a capsule, a suppository or a measured volume of a powder, a granulate, a solution, an emulsion, a suspension, a sol or a gel.

"Unit dose", in the sense of the present invention is a physically-determined unit which contains an individual quantity of active component in combination with a pharmaceutical carrier, the active-principle content of which corresponds to a fraction or multiple of the therapeutic individual dose. An individual dose preferably contains the quantity of active principle which is dispensed in a single application and which corresponds usually to a whole, a half or a third or a quarter of the daily dose. If, for an individual therapeutic administration, only a fraction, such as a half or a quarter, of a unit dose is required, the unit dose is advantageously divisible, for example in the form of a tablet with a notch for breaking.

When the pharmaceutical preparations according to the invention occur in unit doses and are intended for application, for example, to human beings, they contain from 0.5 to 1000, advantageously from 1 to 400 and expecially from 5 to 300, mg of active principle.

Generally speaking, it is advantageous, both in human medicine and in veterinary medicine, to administer the active principle or principles by oral administration in a daily dose of from 0.01 to 40, preferably from 0.1 to 25, especially from 0.1 to 15, mg/kg of body weight, possibly in the form of several, preferably 2 or 3, individual administrations, in order to achieve the desired results. An individual administration contains the active principle or principles in quantities of from 0.01 to 20, preferably from 0.1 to 15 and especially from 0.1 to 10, mg/kg of body weight.

In a parenteral treatment, for example an intramuscular or intravenous application, similar dosages are useful. With this therapy from 50 to 1000 mg of active principle are administered.

The therapeutic administration of pharmaceutical preparation is generally carried out in long-term medication at fixed points of time, such as from 1 to 4 times a day, for example after each meal and/or in the evening. In the case of acute attacks medication is carried out at varying points in time. Under certain circumstances it may be necessary to vary from noted dosages, namely: according to the nature, the body weight and the age of the patient to be treated, the nature and severity of the disease, the nature of the preparation and the application of drug, as well as the period of time or interval within which the administration takes place. Thus in some cases it may be sufficient to manage with less than the previously-mentioned quantity of active principle, whereas in other cases the indicated quantity of active principle must be exceeded. The determination of the optimum dosage and type of application of active principle necessary for each case is made by the expert on the basis of his technical knowledge.

The pharmaceutical preparations ordinarily consist of active principle according to the invention and non-toxic pharmaceutically-compatible drug excipients, which are used in admixture or as diluent in solid, semi-solid or liquid form or as an encapsulating agent, for example in the form of a capsule, a tablet coating, a bag or other container for the therapeutically-active component. An excipient serves, for example, as a vehicle for the uptake of the medicament by the body, as a formulation aid, as a sweetening agent, as a flavor corrector, as a coloring material or as a preservative.

For oral use it is possible to use, for example, tablets, pills, hard and soft capsules (for example of gelatin), dispersible powder, granulates, aqueous and oily suspensions, emulsions, solutions or syrups.

Tablets optionally contain inert diluent, for example calcium carbonate, calcium phosphate, sodium phosphate or lactose; granulating and distributing agents, for example maize starch or alginates; binders, such as starch, gelatin or gum acacia; and lubricants, such as aluminum stearate, magnesium stearate, talcum or silicone oil. They are, e.g., provided with a coating which is optionally designed to provide a delayed dissolution and resorption of the drug in the gastro-intestinal tract and therefore ensures, for example, better capatibility, protraction or retarding. Gelatin capsules, e.g., contain the pharmaceutical product mixed with a solid diluent, for example calcium carbonate or kaolin, or an oily diluent, for example olive oil, groundnut oil or liquid paraffin.

Aqueous suspensions contain, e.g., suspension agents, for example sodium carboxymethylcellulose, methylcellulose, hydroxypropylcellulose, sodium alignate, polyvinylpyrrolidone, gum dragon or gum acacia; dispersants and wetting agents, for example polyoxyethylene stearate, heptadecaethylene oxycetanol, polyoxyethylene sorbitol monooleate, polyoxyethylene sorbitan monooleate or lecithin; preservatives, such as methyl or propyl hydroxybenzoates; flavoring materials; and/or sweetening agents, for example saccharose, lactose, sodium cyclamate, dextrose or invert sugar syrup.

Oily suspensions contain, for example, groundnut oil, olive oil, sesame oil, coconut oil or liquid paraffin and thickeners, such as beeswax, paraffin wax or cetyl alcohol; they also optionally contain sweeteners, flavoring material and anti-oxidant.

Powders and granulates which are dispersible in water optionally contain the pharmaceutical principle in admixture with dispersant, wetting agent and/or suspending agent, for example those previously mentioned, as well as suspension agents, flavoring materials and coloring materials.

Emulsions contain, for example, olive oil, groundnut oil or liquid paraffin, as well as emulsifier, such as gum acacia, gum dragon, phosphatides, sorbitan monooleate or polyoxyethylene sorbitan monooleate, and sweetener and flavoring materials.

For rectal use suppositories containing the pharmaceutical principle are employed; these are produced with binders, for example cocoa butter or polyethyleneglycols, which melt at rectal temperature.

For parenteral use of the pharmaceutical products sterile injectable aqueous suspensions, isotonic saline solutions or other solutions which, e.g., contain dispersants or wetting agents and/or pharmacologically-compatible diluents, for example propyleneglycol or butyleneglycol, are employed.

The active principle or principles are optionally formulated (with one or more carrier materials or additives) also in a micro-encapsulated form.

In addition to N-substituted ω-aminoalkanoyl-ω-aminoalkanoic acid of formula I and/or salts thereof, pharmaceutical preparations optionally contain one or more other pharmacologically-active components of other groups of pharmaceutical products, such as antiacids, for example aluminum hydroxide and magnesium aluminate; tranquilizers, such as benzodiazepines, for example Diazepam; spasmolytics, such as Bietamiverin and Camylofin; anticholinergics, such as Oxyphencyclimine and Phencarbamide; despumation agents, such as dimethylpolysiloxane; laxatives, such as Bisacodyl; swelling agents; possibly also ferments, gallic acids, antibiotics, vitamins, amino acids or fatty acid mixtures.

N-substituted ω-aminoalkanoyl-ω-aminoalkanoic acids of formula I are synthesized, e.g., by reacting an ω-amonoalkanoic acid of formula II (in which $R^1$, $R^2$ and A have their previously-ascribed meanings and, if desired, after conversion into a corresponding acid derivative, such as an acid chloride, azide, azolide, anhydride or ester) with an ω-aminoalkanoic acid of formula III (in which $R^3$ and B have their previously-ascribed meanings).

The reaction of an ω-aminoalkanoic acid of formula II with one of formula III is carried out according to methods which are known to the technician, for example, from peptide chemistry. Illustrative processes include the method of mixed anhydrides, the carbodiimide method, the azide method and the method of activated esters. If desired, amino or carboxyl groups of compounds II and/or III, which are not intended to take part in the reaction, are optionally protected by protective groups (known from peptide chemistry) which are readily split off again after reaction. A general description of these methods is found, inter alia, in H. Beyer, "Lehrbuch der organischen Chemie", S. Hirzel-Verlag, Leipzig (1968); Houben-Weyl, "Methoden der organischen Chemie", 4th edition, volume XV/2, Synthesis of peptides; Synthesis of peptides, part II, published by E. Wünsch, Georg Thieme Verlag Stuttgart (1974); C. H. Bamford et al., "Synthetic Polypeptides, Preparation, Structure and Properties", Academic Press Inc., New York (1956); M. Bodanszky and M. A. Ondetti, "Peptide Synthesis", Interscience Publishers, New York, London, Sydney (1966).

To produce compounds Ia, Ib, Ic, Id and Ie, corresponding starting materials IIa, IIb, IIc, IId or IIe and IIIa, IIIb, IIIc, IIId or IIIe, in which the substituents have their previously-ascribed meanings, are reacted with one another.

The starting aminoalkanoic acids of the formulae II and III are known compounds or are readily produced from available compounds by known processes, such as:

Ethyl p-anisidinoacetate is dissolved in an inert solvent (benzene) and is mixed with an equivalent quantity of p-chlorobenzoyl chloride in the presence of an equivalent quantity of pyridine. The resultant ethyl N-(p-chlorobenzoyl)-p-anisidinoacetate is saponified with alcoholic potash to produce N-(p-chlorobenzoyl)-p-anisidinoacetic acid, melting point: 195° to 197°.

Analogously, N-(p-chlorobenzoyl)-2,6-dimethylanilinoacetic acid, melting point: 182° to 184°, is obtained from ethyl 2,6-dimethylanilinoacetate by reaction with p-chlorobenzoyl chloride and saponification of the reaction product.

Analogous to the process for producing N-benzoyl-β-(p-anisidino)propionic acid [R. C. Elderfield et al, J. Am. Chem. Soc., 68 (1946) 1262–1263] the following compounds are synthesized by reacting the corresponding starting compounds:

N-(p-chlorobenzoyl)-β-(p-anisidino)propionic acid, melting point: 70° to 74°;

N-acetyl-β-(p-anisidino)propionic acid, oil;

N-(p-chlorobenzoyl)-β-(2,6-dimethylanilino)propionic acid, melting point: 162° to 163°.

Analogously, acylation of ethyl α-(p-anisidino)propionate, followed by saponification of the reaction product yields:

N-acetyl-α-(p-anisidino)propionic acid, melting point: 195° to 197°;

N-(p-chlorobenzoyl)-α-(p-anisidino)propionic acid, melting point 164° to 166°;

N-(2,4-dichlorobenzoyl)-α-(p-anisidino)propionic acid, melting point: 143° to 145°;

N-(m-trifluoromethylbenzoyl)-α-(p-anisidino)propionic acid; oil;

N-(α-furoyl)-α-(p-anisidino)propionic acid, melting point: 156° to 158°.

By the acylation of ethyl γ-(2,6-dimethylanilino)butyrate with 3,4,5-trimethoxybenzoyl chloride, followed by saponification, N-(3,4,5-trimethoxybenzoyl)-γ-(2,6-dimethyl anilino)butyric acid, melting point: 134°–136°, is obtained.

Compounds of the formula III, preferably lower alkyl esters, are easily obtained by reacting ω-bromoalkanoic acid esters with primary amines. Acylation yields N-acylamino acid esters, the saponification of which gives free acids of formula II. The following new compounds are thus produced:

Ethyl γ-(p-anisidino)butyrate, melting point: 39° to 40°;

Ethyl γ-(2,6-diethylanilino)butyrate, boiling point: 124° to 126° (0.05 mm Hg);

Ethyl γ-(2-ethyl-6-methylanilino)butyrate, boiling point: 112° to 120° (0.05 mm Hg).

N-(p-chlorobenzoyl)-4-[(1,1,3,3-tetramethylbutyl)amino]-butyric acid, melting point: 141° to 143° {from ethyl 4-bromobutyrate and 1,1,3,3-tetramethylbutylamino)butyrate] with p-chlorobenzoyl chloride to produce ethyl N-(p-chlorobenzoyl)-4-[(1,1,3,3-tetramethylbutyl)amino]butyrate, melting point: 79° to 91°, and saponification};

N-(p-fluorobenzoyl)-4-[(1,1,3,3-tetramethylbutyl)amino]butyric acid, melting point: 114° to 117° {from ethyl 4-bromobutyrate and 1,1,3,3-tetramethylbutylamine, acylation of the ethyl 4-[(1,1,3,3-tetramethylbutyl)amino]butyrate with p-fluorobenzoyl chloride to produce ethyl N-(p-fluorobenzoyl)-4-[(1,1,3,3-tetramethylbutyl)amino]butyrate (viscous oil) and saponification};

N-(p-chlorobenzoyl)-4-(tert.-butylamino)butyric acid, melting point: 126°–127°, [from ethyl 4-bromobutyrate and tert.-butylamine, acylation of the ethyl 4-(tert.-butylamino)butyrate and saponification].

N-(3,4,5-trimethoxybenzoyl)-6-(tert.butylamino)caproic acid, melting point: 83° to 85° [from ethyl 6-bromocaproate and tert.-butylamine, acylation of the ethyl 6-(tert.-butylamino)caproate with 3,4,5-trimethoxybenzoyl chloride to produce ethyl N-(3,4,5-trimethoxybenzoyl)-6-(tert.-butylamino)caproate (viscous oil which cannot be distilled without decomposition) and saponification];

N-(p-chloro)benzoyl-4-[(1,1-dimethylpropyl)amino]butyric acid, melting point: 79° to 81° {from ethyl 4-bromobutyrate and 1,1-dimethylpropylamine, acylation of the ethyl 4-[(1,1-dimethylpropyl)amino]butyrate with p-chlorobenzoyl chloride to produce ethyl N-(p-chlorobenzoyl)-4-[(1,1-dimethylpropyl)amino]butyrate (melting point: 65° to 67°) and saponification};

N-(2,4-dichlorobenzoyl)-4-[(1,1-dimethylpropyl)amino]butyric acid, melting point: 124° to 126° {from ethyl 4-bromobutyrate and 1,1-dimethylpropylamine, acylation, of the ethyl 4-[(1,1-dimethylpropyl)amino]butyrate with 2,4-dichlorobenzoyl chloride to produce ethyl N-(2,4-dichlorobenzoyl)-4-[(1,1-dimethylpropyl)amino]butyrate (melting point 75° to 77°) and saponification};

N-(n-butyryl)-4-[(1,1-dimethylpropyl)amino]butyric acid, melting point: 70° to 72° {from ethyl 4-bromobutyrate and 1,1-dimethylpropylamine, acylation of the ethyl 4-[(1,1-dimethylpropyl)amino]butyrate with n-butyric anhydride to produce ethyl N-(n-butyryl)-4-[(1,1-dimethylpropyl)amino]butyrate (oil) and saponification};

N-(p-chlorobenzoyl)-4-[(2-methyl-3-butyn-2-yl)amino]butyric acid, melting point: 102° to 104° {from ethyl 4-bromobutyric acid and 2-methyl-3-butyn-2-ylamine, acylation of the ethyl 4-[(2-methyl-3-butyn-2-yl)amino]butyrate with p-chlorobenzoyl chloride to form ethyl N-(p-chlorobenzoyl4-[(2-methyl-3-butyn-2-yl)amino]butyrate (melting point 68° to 70°) and saponification};

N-(p-chlorobenzoyl)-4-[(3-ethyl-1-pentyn-3-yl)amino]butyric acid, melting point: 92° to 94° {from ethyl 4-bromobutyrate and 3-ethyl-1-pentyn-3-ylamine, acylation of the ethyl 4-[(3-ethyl-1-pentyn-3-yl)amino]butyrate with p-chlorobenzoyl chloride to form ethyl N-(p-chlorobenzoyl)-4-[(3-ethyl-1-pentyn-3-yl)amino]butyrate (melting point: 73° to 75°) and saponification};

N-(p-chlorobenzoyl-4-(1-ethynylcyclohexyl-1)-aminobutyric acid, melting point: 120° to 122° {from ethyl 4-bromobutyrate and 1-ethynylcyclohexylamine, acylation of the ethyl 4-[(1-ethynylcyclohexyl-1)-amino]butyrate with p-chlorobenzoyl chloride to produce ethyl N-(p-chlorobenzoyl)-4-[(1-ethynylcyclohexyl-1)-amino]butyrate (melting point 84° to 86°) and saponification};

N-acetyl-4-[(1-ethynylcyclohexyl-1)-amino]butyric acid, melting point: 103° to 105° {from ethyl 4-bromobutyrate and 1-ethynylcyclohexylamine, acylation of the ethyl 4-[(1-ethynylcyclohexyl-1)-amino]butyrate with acetyl chloride to produce ethyl N-acetyl-4-[(1-ethynylcyclohexyl-1)-amino]butyrate (melting point 73° to 75°) and saponification};

N-(p-chlorobenozyl)-4-[(1-propylcyclohexyl-1)-amino]butyric acid, melting point: 110° to 112° {from ethyl 4-bromobutyrate and 1-(n-propyl)cyclohexylamine, acylation of the 4-[(1-(n-propyl)cyclohexyl-1)-amino]butyric acid ester with p-chlorobenzoyl chloride to produce ethyl N-(p-chlorobenzoyl)-4-[1-(n-propylcyclohexyl-1)-amino]butyrate (viscous oil which cannot be distilled without decomposition) and saponification};

N-(p-chlorobenzoyl)-4-[1-(n-butylcyclopentyl-1)-amino]butyric acid, melting point: 91° to 93° {from ethyl 4-bromobutyrate and 1-(n-butyl)cyclopentylamine, acylation of the ethyl 4-[1-(n-butylcyclopentyl-1)-amino]butyrate with p-chlorobenzoyl chloride to produce ethyl N-(p-cholorobenzoyl)-4-[1-(n-butyl)-cyclopentyl-1)-amino]butyrate (melting point: 85° to 87°) and saponification};

N-(p-chlorobenzoyl)-4-(1-adamantyl)aminobutyric acid, melting point: 164° to 166° {from ethyl 4-bromobutyrate and 1-aminoadamantane, acylation of the ethyl 4-[(1-adamantyl)amino]butyrate with p-chlorobenzoyl chloride to produce ethyl N-(p-chlorobenzoyl)-4-[(1-adamantyl)-amino]butyrate (melting point: 103° to 105°) and saponification};

N-(p-chlorobenzoyl)-4-cyclooctylaminobutyric acid, melting point: 109° to 110° {from ethyl 4-bromobutyrate and cyclooctylamine, acylation of the ethyl 4-cyclooctylaminobutyrate with p-chlorobenzoyl chloride to produce ethyl N-(p-chlorobenzoyl)-4-cyclooctylaminobutyrate (an oil which is not distillable without decomposition) and saponification};

N-(p-chlorobenzoyl)-4-benzhydrylaminobutyric acid, melting point: 110° to 111° {from ethyl 4-bromobutyrate and benzhydrylamine, acylation of the ethyl 4-benzhydrylaminobutyrate [boiling point: 150° to 155° (0.02 mm Hg)] with p-chlorobenzoyl chloride to produce ethyl N-(p-chlorobenzoyl)-4-benzyhydrylaminobutyrate (melting point: 68° to 69°) and saponification}.

N-acetyl-4-benzhydrylaminobutyric acid, melting point: 173° to 174° [by the acylation of ethyl 4-benzhydrylaminobutyrate with acetyl chloride to produce ethyl N-acetyl-4-benzhydrylaminobutyrate (viscous oil which is not distillable) and saponification];

N-(p-chlorobenzonyl)-4-(1-phenylethylamino)butyric acid, melting point: 110° to 112° [from ethyl 4-bromobutyrate and dl-1-phenylethylamine, acylation of the ethyl 4-(1-phenylethylamino)butyrate with p-chlorobenzoyl chloride to form ethyl N-(p-chlorobenzoyl)-4-(1-phenylethylamino)butyrate (viscous non-distillable oil) and saponification];

N-(p-chlorobenzoyl)-6-(1-phenylethylamino)caproic acid, melting point: 132° to 133° [from ethyl 6-bromocaproate and dl-1-phenylethylamine, acylation of the ethyl 6-(1-phenylethylamino)caproate with p-chlorobenzoyl chloride to produce ethyl N-(p-chloro)benzoyl-6-(1-phenylethylamino)caproate (viscous non-distillable oil) and saponification];

N-(p-chloro)benzoyl-4-homoveratrylaminobutryic acid, melting point 101° to 103° [from ethyl 4-bromobutyrate and homoveratrylamine, acylation of the ethyl 4-homoveratrylaminobutyrate with p-chlorobenzoyl chloride to produce ethyl N-(p-chlorobenzoyl-4-homoveratrylaminobutrate (viscous non-distillable oil) and saponification];

N-(p-chloro)benzoyl-4-[(1,2-diphenylethyl)amino]butyric acid, melting point: 121° to 122° {from ethyl 4-bromobutyrate and 1,2-diphenylethylamine, acylation of the 4-[(1,2-diphenylethylamino]butyric acid ester with p-chlorobenzoyl chloride to produce ethyl N-(p-chlorobenzoyl-4-[(1,2-diphenylethyl)amino]butyrate (viscous non-distillable oil) and saponification};

N-(p-chlorobenzoyl)-4-aminobutyric acid, melting point: 107° to 108° (by acylation of 4-aminobutyric acid with p-chlorobenzoyl chloride in sodium hydroxide solution at pH 7 to 8);

N-(m-trifluoromethylbenzoyl)-4-[(1,1,3,3-tetramethylbutyl)amino]butyric acid, melting point: 86° to 87° {from ethyl 4-bromobutyrate and 1,1,3,3-tetramethylbutylamine, acylation of the ethyl 4-[(1,1,3,3-tetramethylbutyl)amino]butyrate with m-trifluoromethylbenzoyl chloride and saponification};

N-crotonoyl-4-[(1,1,3,3-tetramethylbutyl)amino]butyric acid, melting point: 92° to 93° {from ethyl 4-bromobutyrate and 1,1,3,3-tetramethylbutylamine, acylation of the ethyl 4-[(1,1,3,3-tetramethylbutyl)amino]butyrate with crotonic acid chloride to produce ethyl N-crotonoyl-4-[(1,1,3,3-tetramethylbutyl)amino]butyrate (viscous oil) and saponification};

N-propionyl-4-benzhydrylaminobutyric acid, melting point: 151.5° to 152.5° [by acylation of ethyl 4-benzhydrylaminobutyrate with propionyl chloride to produce ethyl N-propionyl-4-benzhydrylaminobutyrate (melting point: 83° to 85°) and saponification];

N-(5-chloro-2-methoxybenzoyl)-4-benzhydrylaminobutyric acid, melting point: 176° to 178° [by acylation of ethyl 4-benzhydrylaminobutyrate with 5-chloro-2-methoxybenzoic acid chloride to produce ethyl N-(5-chloro-2-methoxybenzoyl)-4-benzhydrylaminobutyrate (viscous non-distillable oil) and saponification];

N-acetyl-6-benzhydrylaminocaproic acid, melting point: 119° to 120° {from ethyl 6-bromocaproate and benzhydrylamine, acylation of the ethyl 6-benzhydrylaminocaproate [boiling point: 162° to 167° (0.02 mm Hg)] with acetyl chloride to produce ethyl N-acetyl-6-benzhydrylaminocaproate (viscous non-distillable oil) and saponification};

N-isobutyryl-6-benzhydrylaminocaproic acid, melting point: 106° to 107° [by acylation of ethyl 6-benzhydrylaminocaproate with isobutyrylchloride to produce ethyl N-isobutyryl-6-benzhydrylaminocaproate (viscous nondistillable oil) and saponification];

N-acetyl-5-benzhydrylaminovaleric acid, melting point: 135° to 136° {from ethyl 5-bromovalerate and benzhydrylamine, acylation of the ethyl 5-benzhydrylaminovalerate [boiling point: 158° to 163° (0.01 mm Hg)] with acetyl chloride to produce ethyl N-acetyl-5-benzhydrylaminovalerate (viscous non-distillable oil) and saponification};

N-crotonoyl-5-benzhydrylaminovaleric acid, melting point: 88° to 89° ]by acylation of ethyl 5-benzhydrylaminovalerate with crotonoyl chloride to produce ethyl N-crotonoyl-5-benzhydrylaminovalerate (viscous nondistillable oil) and saponification].

Starting products or intermediates II are alternatively produced by hydrolysis (saponification) of the corresponding N-$R^2$-lactams, followed by acylation. Examples of the products prepared by this variant are as follows:

N-benzoyl-4-(n-butyl)aminobutyric acid, melting point: 62° to 64° (by saponification of n-butylpyrrolidone with sodium hydroxide, followed by acylation with benzoyl chloride);

N-(p-chlorobenzoyl)-5-(n-butylamino)valeric acid, melting point: 64.5° to 65.5° [by saponification of 1-(n-butyl)-δ-valerolactam with sodium hydroxide, followed by acylation with p-chlorobenzoyl chloride at pH 7 to 8; 1-(n-butyl)-δ-valerolactam (boiling point 122°/13 mm Hg) is obtained by alkylation of δ-valerolactam with 1-bromobutane in anhydrous dimethylsulfoxide in the presence of potassium hydroxide];

N-(p-chlorobenzoyl)-4-benzylaminobutyric acid, melting point: 101° to 102° [by saponification of N-benzyl-pyrrolidone with sodium hydroxide, followed by acylation with p-chlorobenzoyl chloride];

N-(p-chlorobenzoyl)-4-[(p-methoxybenzyl)amino]-butyric acid, melting point: 128.5° to 129.5° [by the saponification of 1-(p-methoxybenzlpyrrolidone with sodium hydroxide, followed by acylation with p-chlorobenzoyl chloride];

N-(p-chlorobenzoyl)-5-benzylaminovaleric acid, melting point: 93° to 94° (by saponification of 1-benzyl-δ-valerolactam with sodium hydroxide, followed by acylation with p-chlorobenzoyl chloride).

The conversion of acids of formula I (or of Ia, Ib, Ic, Id and Ie) to their salts is carried out, e.g., by direct alkaline hydrolysis of a derivative, for example an ester, of an acid of formula I. As alkaline reactant, that inorganic or organic base, whose salt is desired, is employed. However, the salts are also obtained by reacting an acid of formula I (or Ia, Ib, Ic, Id or Ie) with the stoichiometric equivalent of the corresponding base, for example sodium hydroxide or sodium alcoholate, or by converting readilysoluble salts into sparingly-soluble salts by double decomposition, or by converting any salt into a pharmacologically-compatible salt.

The following examples illustrate and explain the invention in greater detail without restricting it. The abbreviations M.P. and B.P. signify melting point and boiling point, respectively; and all temperatures are in °C.

EXAMPLE 1

N-[N-(p-chlorobenzoyl)-4-(2,6-dimethylanilino)-butyryl]-4-(p-anisidino)-butyric acid $R^1$ = p-chlorobenzoyl, $R^2$ = 2,6-dimethylphenyl, $R^3$ = p-methoxyphenyl, A = B = —$CH_2$—$CH_2$—$CH_2$—

(a) 34.6 g of N-(p-chlorobenzoyl)-4-(2,6-dimethylanilino)butyric acid are dissolved in 100 ml of freshly-distilled tetrahydrofuran and mixed with 10.1 g of triethylamine. The solution is cooled to −15° in a cold bath; after adding (drop by drop) 5.4 g of ethyl chloroformate, the stirring is continued for a further 10 minutes at −15°. A solution of 22.3 g of ethyl 4-(p-anisidino)butyrate in 60 ml of tetrahydrofuran is then added at this temperature. The cold bath is then removed, and the stirring is continued for a further 20 hours until evolution of carbon dioxide ceases. The tetrahydrofuran is distilled off in vacuo, and the residue is taken up in ethyl acetate. The ethyl acetate solution is shaken in the order of sequence given: 3 times each with 1 N hydrochloric acid, water and 5% potassium bicarbonate solution and once with water. The organic phase is dried over magnesium sulfate, and the solvent evaporated off. The residue, on evaporation, is recrystallized from ethyl acetate/cyclohexane to yield 44.0 g (75% of theory) of ethyl N-[N-(p-chlorobenzoyl-4-(2,6-dimethylanilino)butyryl]-4-(p-anisidino)butyrate (M.P. 99° to 101°).

(b) A solution of 33.9 g of the ester obtained according to (a) in 200 ml of benzene and a solution of 3.9 g of potassium hydroxide in 40 ml of ethanol are mixed together and then stirred at room temperature (20°) for 12 hours. The solution is shaken out twice with 150 ml of water on each occasion; the aqueous phase is washed with diethyl ether and then acidified with dilute hydrochloric acid. The resultant precipitate is extracted with chloroform. The residue (remaining after distilling off the chloroform) is recrystallized from ethyl acetate to yield 28.7 g (89% of theory) of N-[N-(p-chlorobenzoyl)-4-(2,6-dimethylanilino)butyryl]-4-(p-anisidino)-butyric acid (M.P. 119° to 121°).

EXAMPLE 2

N-[N-(p-chlorobenzoyl)-4-(2,6-dimethylanilino)-butyryl]-4-(2,6-dimethylanilino)butyric acid $R^1$ = p-chlorobenzoyl, $R^2$ = $R^3$ = 2,6-dimethylphenyl, A = B = —$CH_2$—$CH_2$—$CH_2$—

Analogously to Example 1, using equivalent quantities, reacting N-(p-chlorobenzoyl)-4-(2,6-dimethylanilino)butyric acid and ethyl 4-(2,6-dimethylanilino)butyrate and suitable processing produces ethyl N-[N-(p-chlorobenzoyl)-4-(2,6-dimethylanilino)-butyryl]-4-(2,6-dimethylanilino)butyrate (M.P. 95° to 97°), the saponification of which and the processing of the reaction product yields N-[N-(p-chlorobenzoyl)-4-(2,6-dimethylanilino)butyryl]-4-(2,6-dimethylanilino)-butyric acid (M.P. 129° to 131°).

EXAMPLE 3

N-[N-(p-chlorobenzoyl)-4-(p-anisidino)butyryl]-4-(2,6-dimethylanilino)-butyric acid $R^1$ = p-chlorobenzoyl, $R^2$ = p-methoxyphenyl, $R^3$ = 2,6-dimethylphenyl, A = B = —$CH_2$—$CH_2$—$CH_2$—

Analogously to Example 1, by using equivalent quantities, reacting N-(p-chlorobenzoyl)-4-(p-anisidino)-butyric acid and ethyl 4-(2,6-dimethylanilino)butyrate and suitable processing produces ethyl N-[N-(p-chlorobenzoyl)-4-(p-anisidino)butyryl]-4-(2,6-dimethylanilino)butyrate (oil), saponification of which and the processing of the reaction product yields N-[N-(p-chlorobenzoyl)-4-(p-anisidino)butyryl]-4-(2,6-dimethylanilino)butyric acid (M.P. 131° to 133°).

EXAMPLE 4

N-[N-(p-chlorobenzoyl)-4-(p-anisidino)butyryl]-4-(p-anisidino)butyric acid $R^1$ = p-chlorobenzoyl, $R^2$ = $R^3$ = p-methoxyphenyl, A = B = —$CH_2$—$CH_2$—$CH_2$—

Analogously to Example 1, by using equivalent quantities, reacting N-(p-chlorobenzoyl)-4-(p-anisidino)-butyric acid and methyl N-(p-chlorobenzoyl-4-(p-anisidino)butyrate and suitable processing produces methyl N-[N-(p-chlorobenzoyl)-4-(p-anisidino)-butyryl]-4-(p-anisidino)butyrate (oil), saponification of which and processing of the reaction product yields N-[N-(p-chlorobenzoyl)-4-(p-anisidino)butyryl]-4-(p-anisidino)butyric acid (M.P. 62° to 64°).

EXAMPLE 5

N-[N-(p-chlorobenzoyl)-4-(2,6-dimethylanilinobutyryl]-4-aminobutyric acid $R^1$ = p-chlorobenzoyl, $R^2$ = 2,6-dimethylphenyl, $R^3$ = —H, A = B = —$CH_2$—$CH_2$—$CH_2$—

Analogously to Example 1, by using equivalent quantities, reacting N-(p-chlorobenzoyl)-4-(2,6-dimethylanilino)butyric acid and methyl 4-aminobutyrate and suitable processing produces methyl N-[N-(p-chlorobenzoyl)-4-(2,6-dimethylanilino)butyryl]-4-aminobutyrate (oil), saponification of which and processing of the reaction product yields N-[N-(p-chlorobenzoyl)-4-(2,6-dimethylanilino)butyryl]-4-aminobutyric acid (M.P. 141° to 142°).

EXAMPLE 6

N-[N-(3,4,5-trimethoxybenzoyl)-4-(2,6-dimethylanilino)butyryl]-4-aminobutyric acid $R^1$=3,4,5-trimethoxybenzoyl, $R^2$=2,6-dimethylphenyl, $R^3$=—H, A=B=—CH$_2$—CH$_2$—CH$_2$ Analogously to Example 1, by using equivalent quantities, reacting N-(3,4,5-trimethoxybenzoyl)-4-(2,6-dimethylanilino)butyric acid and methyl 4-aminobutyrate and suitable processing produces methyl N-[N-(3,4,5-trimethoxybenzoyl)-4-(2,6-dimethylanilino)-butyryl]-4-aminobutyrate (M.P. 97° to 99°), saponification of which and processing of the reaction product yields N-[N-(3,4,5-trimethoxybenzoyl)-4-(2,6-dimethylanilino)butyryl]-4-aminobutyric acid (M.P. 100° to 101°).

EXAMPLE 7

N-[N-(p-chlorobenzoyl)-3-(p-anisidino)propionyl]-4-(p-anisidino)butyric acid $R^1$=p-chlorobenzoyl, $R^2$=$R^3$=p-methoxyphenyl, A=—CH$_2$—CH$_2$—, B=—CH$_2$—CH$_2$—CH$_2$—

Analogously to Example 1, by using equivalent quantities, reacting N-(p-chlorobenzoyl)-3-(p-anisidino)propionic acid and methyl 4-(p-anisidino)butyrate and suitable processing produces methyl N-[N-(p-chlorobenzoyl)-3-(p-anisidino)propionyl]-4-(p-anisidino)butyrate (oil), saponification of which and processing of the reaction product yields N-[N-(p-chlorobenzoyl)-3-(p-anisidino)propionyl]-4-(p-anisidino)butyric acid (M.P. 91° to 93°).

EXAMPLE 8

N-[N-(p-chlorobenzoyl)-3-(2,6-dimethylanilino)propionyl]-4-(p-anisidino)butyric acid $R^1$=p-chlorobenzoyl, $R^2$=2,6-dimethylphenyl, $R^3$=p-methoxyphenyl, A=—CH$_2$—CH$_2$—, B=—CH$_2$—CH$_2$—CH$_2$—

Analogously to Example 1, by using equivalent quantities, reacting N-(p-chlorobenzoyl)-3-(2,6-dimethylanilino)propionic acid and methyl 4-(p-anisidino)butyrate and suitable processing produces methyl N-[N-p-chlorobenzoyl)-3-(2,6-dimethylanilino)-propionyl]-4-(p-anisidino)butyrate (oil), saponification of which and processing of the reaction product yields N-[N-(p-chlorobenzoyl)-3-(2,6-dimethylanilino)propionyl]-4-(p-anisidino)butyric acid (M.P. 138° to 140°).

EXAMPLE 9

N-[N-acetyl-3-(2,6-dimethylanilino)propionyl]-4-(p-anisidino)butyric acid $R^1$=CH$_3$—CO—, $R^2$=2,6-dimethylphenyl, $R^3$=p-methoxyphenyl, A=—CH$_2$—CH$_2$—, B=—CH$_2$—CH$_2$—CH$_2$—

Analogously to Example 1, by using equivalent quantities, reacting N-acetyl-3-(2,6-dimethylanilino)propionic acid and methyl 4-(p-anisidino)butyrate and suitable processing produces methyl N-[N-acetyl-3-(2,6-dimethylanilino)propionyl]-4-(p-anisidino)butyrate (oil), saponification of which and processing of the reaction product yields N-[N-acetyl-3-(2,6-dimethylanilino)propionyl]-4-(p-anisidino)butyric acid (M.P. 90° to 92°).

EXAMPLE 10

N-[N-acetyl-3-(2,6-dimethylanilino)propionyl]-4-(2,6-diethylanilino)butyric acid $R^1$=CH$_3$—CO—, $R^2$=2,6-dimethylphenyl, $R^3$=2,6-diethylphenyl A=—CH$_2$—CH$_2$—, B=—CH$_2$—CH$_2$—CH$_2$—

Analogously to Example 1, by using equivalent quantities, reacting N-acetyl-3-(2,6-dimethylanilino)propionic acid and ethyl 4-(2,6-diethylanilino)butyrate and suitable processing produces ethyl N-[N-acetyl-3-(2,6-dimethylanilino)propionyl]-4-(2,6-diethylanilino)butyrate (oil), saponification of which and processing of the reaction product yields N-[N-acetyl-3-(2,6-dimethylanilino)propionyl]-4-(2,6-diethylanilino)butyric acid (M.P. 110° to 111°).

EXAMPLE 11

N-[N-acetyl-3-(2,6-dimethylanilino)propionyl]-4-(2-ethyl-6-methylanilino)butyric acid $R^1$=CH$_3$—CO—, $R^2$=2,6-dimethylphenyl, $R^3$=2-ethyl-6-methylphenyl, A=—CH$_2$—CH$_2$—, B=—CH$_2$—CH$_2$—CH$_2$—

Analogously to Example 1, by using equivalent quantities, reacting N-acetyl-3-(2,6-dimethylanilino)propionic acid and ethyl 4-(2-ethyl-6-methylanilino)butyrate and suitable processing produces ethyl N-[N-acetyl-3-(2,6-dimethylanilino)propionyl]-4-(2-ethyl-6-methylanilino)butyrate (oil), saponification of which and processing of the reaction product yields N-[N-acetyl-3-(2,6-dimethylanilino)propionyl]-4-(2-ethyl-6-methylanilino)butyric acid (M.P. 139° to 141°).

EXAMPLE 12

N-[N-(p-chlorobenzoyl)-2-(2,6-dimethylanilino)acetyl]-4-(2,6-dimethylanilino)butyric acid $R^1$=p-chlorobenzoyl, $R^2$=$R^3$=2,6-dimethylphenyl, A=—CH$_2$—, B=—CH$_2$—CH$_2$—CH$_2$—

Analogously to Example 1, by using equivalent quantities, reacting N-(p-chlorobenzoyl)-2-(2,6-dimethylanilino)acetic acid and ethyl 4-(2,6-dimethylanilino)butyrate and suitable processing produces ethyl N-[N-(p-chlorobenzoyl)-2-(2,6-dimethylanilino)acetyl]-4-(2,6-dimethylanilino)butyrate (M.P. 150° to 151°), saponification of which and processing of the reaction product yields N-[N-(p-chlorobenzoyl)-2-(2,6-dimethylanilino)acetyl]-4-(2,6-dimethylanilino) butyric acid (M.P. 214° to 216°).

EXAMPLE 13

N-[N-(p-chlorobenzoyl)-2-(p-anisidino)acetyl]-4-(p-anisidino)butyric acid $R^1$=p-chlorobenzoyl, $R^2$=$R^3$=p-methoxyphenyl, A=—CH$_2$—, B=—CH$_2$—CH$_2$—CH$_2$—

Analogously to Example 1, by using equivalent quantities, reacting N-(p-chlorobenzoyl)-2-(p-anisidino)acetic acid and methyl 4-(p-anisidino)butyrate and suitable processing produces methyl N-[N-(p-chlorobenzoyl)-2-(p-anisidino)acetyl]-4-(p-anisidino)butyrate (oil), saponification of which and processing of the reaction product yields N-[N-(p-chlorobenzoyl)-2-(p-anisidino)acetyl]-4-(p-anisidino)butyric acid (M.P. 105° to 108°).

EXAMPLE 14

N-[N-acetyl-2-(p-anisidino)acetyl]-4-(p-anisidino)butyric acid $R^1 = CH_3—CO—$,
$R^2 = R^3 = $ p-methoxyphenyl, $A = —CH_2—$,
$B = —CH_2—CH_2—CH_2—$ Analogously to Example 1, by using equivalent quantities, reacting N-(acetyl)-2-(p-anisidino)acetic acid and methyl 4-(p-anisidino)butyrate and suitable processing produces methyl N-[N-(acetyl)-2-(p-anisidino)acetyl]-4-(p-anisidino)butyrate (oil), saponification of which and processing of the reaction product yields N-[N-acetyl-2-(p-anisidino)acetyl]-4-(p-anisidino)butyric acid (M.P. 97° to 100°).

EXAMPLE 15

N-[N-(p-chlorobenzoyl)-2-(p-anisidino)propionyl]-4-(p-anisidino)butyric acid $R^1 = $ p-chlorobenzoyl, $R^2 = R^3 = $ p-methoxyphenyl,
$A = —CH(R^4)—$, $R^4 = —CH_3$,
$B = —CH_2—CH_2—CH_2—$ Analogously to Example 1, by using equivalent quantities, reacting N-(p-chlorobenzoyl)-2-(p-anisidino)propionic acid and methyl 4-(p-anisidino)butyrate and suitable processing produces methyl N-[N-(p-chlorobenzoyl)-2-(p-anisidino)propionyl]-4-(p-anisidino)butyrate (oil), saponification of which and processing of the reaction product yields N-[N-(p-chlorobenzoyl)-2-(p-anisidino)propionyl]-4-(p-anisidino)butyric acid (M.P. 135° to 137°).

EXAMPLE 16

N-[N-(2,4-dichlorobenzoyl)-2-(p-anisidino)propionyl]-4-(p-anisidino)butyric acid $R^1 = $ 2,4-dichlorobenzoyl, $R^2 = R^3 = $ p-methoxyphenyl,
$A = —CH(R^4)—$, $R^4 = —CH_3$,
$B = —CH_2—CH_2—CH_2—$ Analogously to Example 1, by using equivalent quantities, reacting N-(2,4-dichlorobenzoyl)-2-(p-anisidino)propionic acid and methyl 4-(p-anisidino)butyrate and suitable processing produces methyl N-[N-(2,4-dichlorobenzoyl)-2-(p-anisidino)propionyl]-4-(p-anisidino)butyrate (oil), saponification of which and processing of the reaction product yields N-[N-(2,4-dichlorobenzoyl)-2-(p-anisidino)propionyl]-4-(p-anisidino)butyric acid (M.P. 159° to 160°).

EXAMPLE 17

N-[N-acetyl-2-(p-anisidino)propionyl]-4-(p-anisidino)butyric acid $R^1 = CH_3—CO—$,
$R^2 = R^3 = $ p-methoxyphenyl, $A = —CH(R^4)—$,
$R^4 = —CH_3$, $B = —CH_2—CH_2—CH_2—$ Analogously toExample 1, by using equivalent quantities, reacting N-acetyl-2-(p-anisidino)propionic acid and methyl 4-(p-anisidino)butyrate and suitable processing produces methyl N-[N-acetyl-2-(p-anisidino)propionyl]-4-(p-anisidino)butyrate (M.P. 111° to 113°), saponification of which and processing of the reaction produce yields N-[N-acetyl-2-(p-anisidino)propionyl]-4-(p-anisidino)butyric acid (M.P. 155° to 157°).

EXAMPLE 18

N-[N-(m-trifluoromethylbenzoyl)-2-(p-anisidino)propionyl]-4-(p-anisidino)butyric acid $R^1 = $ m-trifluoromethylbenzoyl,
$R^2 = R^3 = $ p-methoxyphenyl, $A = —CH(R^4)—$,
$R^4 = —CH_3$, $B = —CH_2—CH_2—CH_2—$ Analogously to Example 1, by using equivalent quantities, reacting N-(m-trifluoromethylbenzoyl)-2-(p-anisidino)propionic acid and methyl 4-(p-anisidino)butyrate and suitable processing produces methyl N-[N-(m-trifluoromethylbenzoyl)-2-(p-anisidino)propionyl]-4-(p-anisidino)butyrate (oil), saponification of which and processing of the reaction product yields N-[N-(m-trifluoromethylbenzoyl)2-(p-anisidino)propionyl]-4-(p-anisidino)butyric acid (M.P. 119° to 121°).

EXAMPLE 19

N-[N-(2-furoyl)-2-(p-anisidino)propinoyl]-4-(p-anisidino)butyric acid $R^1 = $ 2-furoyl, $R^2 = R^3 = $ p-methoxyphenyl,
$A = —CH(R^4)—$, $R^4 = —CH_3$,
$B = —CH_2—CH_2—CH_2—$ Analogously to Example 1, by using equivalent quantities, reacting N-(2-furoyl)-2-(p-anisidino)propionic acid and methyl 4-(p-anisidino)butyrate and suitable processing produces methyl N-[N-(2-furoyl)-2-(p-anisidino)propionyl]-4-(p-anisidino)butyrate (oil), saponification of which and processing of the reaction product yields N-[N-(2-furoyl)-2-(p-anisidino)propionyl]-4-(p-anisidino)butyric acid (M.P. 204° to 206°).

EXAMPLE 20

N-[N-(p-methoxybenzoyl)-L-phenylalanyl]-4-(p-anisidino)butyric acid $R^1 = $ p-methoxybenzoyl, $R^2 = —H$,
$R^3 = $ p-methoxyphenyl, $A = —CH(R^4)—$, $R^4 = $ benzyl,
$B = —CH_2—CH_2—CH_2—$ Analogously to Example 1, by using equivalent quantities, reacting N-(p-methoxybenzoyl)-L-phenylalantine and methyl 4-(p-anisidino)butyrate and suitable processing produces methyl N-[N-(p-methoxybenzoyl)-L-phenylalanyl]-4-(p-anisidino)butyrate (oil), saponification of which and processing of the reaction product yields N-[N-(p-methoxybenzoyl)-L-phenylalanyl]-4-(p-anisidino)butyric acid (M.P. 143° to 145°).

EXAMPLE 21

N-[N-(p-chlorobenzoyl)phenylalanyl]-4-(p-anisidino)butyric acid $R^1 = $ p-chlorobenzoyl, $R^2 = $ -H, $R^3 = $ p-methoxyphenyl,
$A = —CH(R^4)—$, $R^4 = $ benzyl,
$B = —CH_2—CH_2—CH_2—$ Analogously to Example 1, by using equivalent quantities, reacting N-(p-chlorobenzoyl)phenylalanine and methyl 4-(p-anisidino)butyrate and suitable processing produces methyl N-[N-(p-chlorobenzoyl)phenylalanyl]-4-(p-anisidino)butyrate (oil), saponification of which and processing of the reaction product yields N-[N-(p-chlorobenzoyl)phenylalanyl]-4-(p-anisidino)butyric acid (M.P. 163° to 165°).

EXAMPLE 22

N-[N-(p-chlorobenzoyl)-L-methionyl]-4-(p-anisidino)-butyric acid $R^1$=p-chlorobenzoyl, $R^2$=—H,
$R^3$=p-methoxyphenyl, A=—CH($R^4$)—,
$R^4$=CH$_3$—S—CH$_2$—CH$_2$—,
B=—CH$_2$—CH$_2$—CH$_2$—

Analogously to Example 1, by using equivalent quantities, reacting N-(p-chlorobenzoyl)-L-methionine and 4-(p-anisidino)butyric acid and suitable processing produces methyl N-[N-(p-chlorobenzoyl)-L-methionyl]-4-(p-anisidino)butyrate (oil), saponification of which and processing of the reaction product yields N-[N-(p-chlorobenzoyl)-L-methionyl]-4-(p-anisidino)butyric acid (M.P. 150° to 152°).

EXAMPLE 23

N-[N-(p-chlorobenzoyl)-3-(p-anisidino)propionyl]-3-aminopropionic acid $R^1$=p-chlorobenzoyl, $R^2$=p-methoxyphenyl,
$R^3$=—H, A=B=—CH$_2$—CH$_2$—

Analogously to Example 1, by using equivalent quantities, reacting N-(p-chlorobenzoyl)-3-(p-anisidino)propionic acid and ethyl 3-aminopropionate and suitable processing produces ethyl N-[N-(p-chlorobenzoyl)-3-(p-anisidino)propionyl]-3-aminopropionate (oil), saponification of which and processing of the reaction product yields N-[N-(p-chlorobenzoyl)-3-(p-anisidino)propionyl]-3-aminopropionic acid (M.P. 171° to 172°).

EXAMPLE 24

N-[N-(p-chlorobenzoyl)-4-(2,6-dimethylanilino)-butyryl]-L-alanine $R^1$=p-chlorobenzoyl, $R^2$=2,6-dimethylphenyl,
$R^3$=—H, A=—CH$_2$—CH$_2$—CH$_2$—, B=—CH($R^5$)—,
$R^5$=—CH$_3$ Analogously to Example 1, by using equivalent quantities, reacting N-(p-chlorobenzoyl)-4-(2,6-dimethylanilino)butyric acid and methyl L-alaninate and suitable processing produces methyl N-[N-(p-chlorobenzoyl)-4-(2,6dimethylanilino)butyryl]-L-alaninate (M.P. 91° to 92°), saponification of which and processing of the reaction product yields N-[N-(p-chlorobenzoyl)-4-(2,6-dimethylanilino)butyryl]-L-alanine (M.P. 159° to 161°).

EXAMPLE 25

N-[N-(p-chlorobenzoyl)-4-(2,6-dimethylanilino)-butyryl]glycine $R^1$=p-chlorobenzoyl, $R^2$=2,6-dimethylphenyl,
$R^3$=—H, A=—CH$_2$—CH$_2$—CH$_2$—, B=—CH$_2$—

Analogously to Example 1, by using equivalent quantities, reacting N-(p-chlorobenzoyl)-4-(2,6-dimethylanilino)butyric acid and ethyl glycinate and suitable processing produces ethyl N-[N-(p-chlorobenzoyl)-4-(2,6-dimethylanilino)butyryl]glycinate (oil), saponification of which and processing of the reaction product yields N-[N-(p-chlorobenzoyl)-4-(2,6-dimethylanilino)butyryl]glycine (M.P. 141° to 142°).

EXAMPLE 26

N-[N-(p-chlorobenzoyl)-4-(2,6-dimethylanilino)-butyryl]sarcosine $R^1$=p-chlorobenzoyl, $R^2$=2,6-dimethylphenyl,
$R^3$=—CH$_3$, A=—CH$_2$—CH$_2$—CH$_2$—, B=—CH$_2$—

Analogously to Example 1, by using equivalent quantities, reacting N-(p-chlorobenzoyl)-4-(2,6-dimethylanilino)butyric acid and ethyl sarcosinate and suitable processing produces ethyl N-[N-(p-chlorobenzoyl)-4-(2,6-dimethylanilino)butyryl]sarcosinate (oil), saponification of which and processing of the reaction product yields N-[N-(p-chlorobenzoyl)-4-(2,6-dimethylanilino)butyryl]sarcosine (M.P. 103° to 105°).

EXAMPLE 27

N-[N-(p-chlorobenzoyl)-4-(p-anisidino)butyryl]glycine $R^1$=p-chlorobenzoyl, $R^2$=p-methoxyphenyl,
$R^3$=—H, A=—CH$_2$—CH$_2$—CH$_2$—, B=—CH$_2$—

Analogously to Example 1, by using equivalent quantities, reacting N-(p-chlorobenzoyl)-4-(p-anisidino)butyric acid and ethyl glycinate and suitable processing produces ethyl N-[N-(p-chlorobenzoyl)-4-(p-anisidino)butyryl]glycinate (oil), saponification of which and processing of the reaction product yields N-[N-(p-chlorobenzoyl)-4-(p-anisidino)butyryl]glycine (viscous oil).

EXAMPLE 28

N-[N-(p-chlorobenzoyl)-4-(2,6-dimethylanilino)-butyryl]-L-phenylalanine $R^1$=p-chlorobenzoyl, $R^2$=2,6-dimethylphenyl,
$R^3$=—H, A=—CH$_2$—CH$_2$—CH$_2$—, B=—CH($R^5$)—,
$R^5$=benzyl Analogously to Example 1, by using equivalent quantities, reacting N-(p-chlorobenzoyl)-4-(2,6-dimethylanilino)butyric acid and ethyl L-phenylalaninate and suitable processing produces ethyl N-[N-(p-chlorobenzoyl)-4-(2,6-dimethylanilino)butyryl]-L-phenylalaninate (oil), saponification of which and processing of the reaction product yields N-(p-chlorobenzoyl)-4-(2,6-dimethylanilino)butyryl-L-phenylalanine (M.P. 153° to 155°).

EXAMPLE 29

N-[N-(p-chlorobenzoyl)-4-(2,6-dimethylanilino)-butyryl]-L-serine $R^2$=p-chlorobenzoyl, $R^2$=2,6-dimethylphenyl,
$R^3$=—H, A=—CH$_2$—CH$_2$—CH$_2$—, B=—CH($R^5$)—,
$R^5$=—CH$_2$—OH Analogously to Example 1, by using equivalent quantities, reacting N-(p-chlorobenzoyl)-4-(2,6-dimethylanilino)butyric acid and ethyl L-serinate and suitable processing produces ethyl N-[N-(pchlorobenzoyl)-4-(2,6-dimethylanilino)butyryl]-L-serinate (oil), saponification of which and processing of the reaction product yields N-[N-(p-chlorobenzoyl)-4-(2,6-dimethylanilino)-butyryl]-L-serine (M.P. 147° to 148°).

EXAMPLE 30

N-[N-(p-chlorobenzoyl)-3-(p-anisidino)propionyl]sarcosine $R^1$=p-chlorobenzoyl, $R^2$=p-methoxyphenyl, $R^3$=—CH$_3$, A=—CH$_2$—CH$_2$—, B=—CH$_2$—

Analogously to Example 1, by using equivalent quantities, reacting N-(p-chlorobenzoyl)-3-(p-anisidino)propionic acid and ethyl sarcosinate and suitable processing produces ethyl N-[N-(p-chlorobenzoyl)-3-(p-anisidino)propionyl]sarcosinate (M.P. 104° to 106°), saponification of which and processing of the reaction product yields N-[N-(p-chlorobenzoyl)-3-(p-anisidino)propionyl]sarcosine (M.P. 129° to 131°).

EXAMPLE 31

N-[N-(p-chlorobenzoyl)-3-(p-anisidino)propionyl]glycine $R^1$=p-chlorobenzoyl, $R^2$=p-methoxyphenyl, $R^3$=—H, A=—CH$_2$—CH$_2$—, B=—CH$_2$—

Analogously to Example 1, by using equivalent quantities, reacting N-(p-chlorobenzoyl)-3-(p-anisidino)propionic acid and ethyl glycinate and suitable processing produces ethyl N-[N-(p-chlorobenzoyl)-3-(p-anisidino)propionyl]glycinate (M.P. 87° to 89°), saponification of which and processing of the reaction product yields N-[N-(p-chlorobenzoyl)-3-(p-anisidino)propionyl]glycine (M.P. 185° to 187°).

EXAMPLE 32

N-[N-(p-chlorobenzoyl)-2-(p-anisidino)acetyl]sarcosine $R^1$=p-chlorobenzoyl, $R^2$=p-methoxyphenyl, $R^3$=—CH$_3$, A=B=—CH$_2$—

Analogously to Example 1, by using equivalent quantities, reacting N-(p-chlorobenzoyl)-2-(p-anisidino)acetic acid and ethyl sarcosinate and suitable processing produces ethyl N-[N-(p-chlorobenzoyl)-2-(p-anisidino)acetyl]sarcosinate (oil), saponification of which and processing of the reaction product yields N-[N-(p-chlorobenzoyl)-2-(p-anisidino)acetyl]sarcosine (M.P. 146° to 148°).

EXAMPLE 33

N-[N-(p-chlorobenzoyl)-2-(p-anisidino)acetyl]glycine $R^1$=p-chlorobenzoyl, $R^2$=p-methoxyphenyl, $R^3$=—H, A=B=—CH$_2$—

Analogously to Example 1, by using equivalent quantities, reacting N-(p-chlorobenzoyl)-2-(p-anisidino)acetic acid and ethyl glycinate and suitable processing produces ethyl N-[N-(p-chlorobenzoyl)-2-(p-anisidino)acetyl]glycinate (oil), saponification of which and processing of the reaction product yields N-[N-(p-chlorobenzoyl)-2-(p-anisidino)acetyl]glycine (M.P. 138° to 140°).

EXAMPLE 34

N-[N-(p-chlorobenzoyl)-2-(p-anisidino)acetyl]-3-aminopropionic acid $R^1$=p-chlorobenzoyl, $R^2$=p-methoxyphenyl, $R^3$=—H, A=—CH$_2$—, B=—CH$_2$—CH$_2$—

Analogously to Example 1, by using equivalent quantities, reacting N-(p-chlorobenzoyl)-2-(p-anisidino)acetic acid and ethyl 3-aminopropionate and suitable processing produces ethyl N-[N-(p-chlorobenzoyl)-2-(p-anisidino)acetyl]-3-aminopropionate (oil), saponification of which and processing of the reaction product yields N-[N-(p-chlorobenzoyl)-2-(p-anisidino)acetyl]-3-aminopropionic acid (M.P. 129° to 131°).

EXAMPLE 35

N-[N-(p-chlorobenzoyl)-2-(2,6-dimethylanilino)acetyl]glycine $R^1$=p-chlorobenzoyl, $R^2$=2,6-dimethylphenyl, $R^3$=—H, A=B=—CH$_2$—

Analogously to Example 1, by using equivalent quantities, reacting N-(p-chlorobenzoyl)-2-(2,6-dimethylanilino)acetic acid and ethyl glycinate and suitable processing produces ethyl N-[N-(p-chlorobenzoyl)-2-(2,6-dimethylanilino)acetyl]glycinate (M.P. 127° to 129°), saponification of which and processing of the reaction product yields N-[N-(p-chlorobenzoyl)-2-(2,6-dimethylanilino)acetyl]glycine (M.P. 200° to 201°).

EXAMPLE 36

N-[N-(p-chlorobenzoyl)-2-(2,6-dimethylanilino)acetyl]-3-aminopropionic acid $R^1$=p-chlorobenzoyl, $R^2$=2,6-dimethylphenyl, $R^3$=—H, A=—CH$_2$—, B=—CH$_2$—CH$_2$—

Analogously to Example 1, by using equivalent quantities, reacting N-(p-chlorobenzoyl)-2-(2,6-dimethylanilino)acetic acid and ethyl 3-aminopropionate and suitable processing produces ethyl N-[N-(p-chlorobenzoyl)-2-(2,6-dimethylanilino)acetyl]aminopropionate (M.P. 91° to 92°), saponification of which and processing of the reaction product yields N-[N-(p-chlorobenzoyl)-2-(2,6-dimethylanilino)acetyl]-3-aminopropionic acid. (M.P. 154° to 156°).

EXAMPLE 37

N[N-(p-chlorobenzoyl)-4-(2,6-dimethylanilino)butyryl]-L-proline $R^1$=p-chlorobenzoyl, $R^2$=2,6-dimethylphenyl, A=—CH$_2$—CH$_2$—CH$_2$—, B=—CH($R^5$)—, $R^3$+$R^5$=—CH$_2$—CH$_2$—CH$_2$—

Analogously to Example 1, by using equivalent quantities, reacting N-(p-chlorobenzoyl)-4-(2,6-dimethylanilino)butyric acid and ethyl L-prolinate and suitable processing produces ethyl N-[N-(p-chlorobenzoyl)-4-(2,6-dimethylanilino)butyryl]-L-prolinate (oil), saponification of which and processing of the reaction product yields N-[N-p-chlorobenzoyl)-4-(2,6-dimethylanilino)butyryl]-L-proline (M.P. 129° to 131°).

EXAMPLE 38

N-[N-(p-chlorobenzoyl)-2-(2,6-dimethylanilino)acetyl]-L-proline $R^1$=p-chlorobenzoyl, $R^2$=2,6-dimethylphenyl, A=—CH$_2$—, B=—CH($R^5$)—, $R^3$+$R^5$=—CH$_2$—CH$_2$—CH$_2$—

Analogously to Example 1, by using equivalent quantities, reacting N-(p-chlorobenzoyl)-2-(2,6-dimethylanilino)acetic acid and ethyl L-prolinate and suitable processing produces ethyl N-[N-(p-chlorobenzoyl)-2-(2,6-dimethylanilino)acetyl]-L-prolinate (oil), saponification of which and processing of the reaction product yields N-[N-(p-chlorobenzoyl)-2-(2,6-dimethylanilino)acetyl]-L-proline (M.P. 199°).

EXAMPLE 39

N-[N-(p-chlorobenzoyl)-4-(p-anisidino)butyryl]-6-(benzhydrylamino)hexanoic acid $R^1$=p-chlorobenzoyl, $R^2$=p-methoxyphenyl,
$R^3$=benzhydryl, A=—$CH_2$—$CH_2$—$CH_2$—,
B=—$CH_2$—$CH_2$—$CH_2$—$CH_2$—$CH_2$—

Analogously to Example 1, by using equivalent quantities, reacting N-(p-chlorobenzoyl)-4-(p-anisidino)butyric acid and ethyl 6-(benzhydrylamino)hexanoate and suitable processing produces ethyl N-[N-(p-chlorobenzoyl)-4-(p-anisidino)butyryl]-6-(benzhydrylamino)hexanoate (oil), saponification of which and processing of the reaction product yields N-[N-(p-chlorobenzoyl)-4-(p-anisidino)butyryl]-6-(benzhydrylamino)hexanoic acid (oil).

EXAMPLE 40

N-[N-(propionyl)-4-(2,6-dimethylanilino)butyryl]-4-(benzylamino)butyric acid $R^1$=$CH_3$—$CH_2$—CO—, $R^2$=2,6-dimethylphenyl,
$R^3$=benzyl, A=B=—$CH_2$—$CH_2$—$CH_2$—

Analogously to Example 1, by using equivalent quantities, reacting N-propionyl-4-(2,6-dimethylanilino)butyric acid and ethyl 4-(benzylamino)butyrate and suitable processing produces ethyl N-[N-propionyl-4-(2,6-dimethylanilino)butyryl]-4-(benzylamino)butyrate (oil), saponification of which and processing of the reaction product yields N-[N-propionyl-4-(2,6-dimethylanilino)butyryl]-4-(benzylamino)butyric acid (oil).

EXAMPLE 41

N-[N-(p-chlorobenzoyl)-4-(p-anisidino)butyryl]-4-(p-anisidino)butyric acid $R^1$=p-chlorobenzoyl, $R^2$=$R^3$=p-methoxyphenyl,
A=B=—$CH_2$—$CH_2$—$CH_2$ A solution of 34.8 g of N-(p-chlorobenzoyl)-4-(p-anisidino)butyric acid in 100 ml of benzene is mixed with 35.7 g of thionyl chloride and a drop of pyridine and then heated to boiling under reflux for 1 hour. The solvent is distilled off in vacuo, and the residue (35.9 g) is dissolved in 60 ml of benzene. This solution is mixed with a solution of 22.5 g of methyl 4-(p-anisidino)butyrate and 13.5 g of ethyo diisopropylamine in 150 ml of benzene and is stirred for 30 minutes at room temperature. The precipitated deposit is filtered off, and the filtrate concentrated by evaporation. The evaporation residue (56.0 g) is dissolved in 100 ml of methanol and, after the addition of a solution of 8.5 g of potassium hydroxide in 100 ml of ethanol, is stirred for 2 hours at room temperature. The solvent is distilled off in vacuo, the residue is dissolved in water and the aqueous solution is weakly acidified with dilute hydrochloric acid. The separated product is extracted with diethyl ether, and the evaporated ether extract is purified by column chromatography (adsorbent: silica gel; eluent: chloroform). By evaporation of the solvent 25.9 g (48 percent of theory) of N-[N-(p-chlorobenzoyl)-4-(p-anisidino)butyryl]-4-(p-anisidino)butyric acid is obtained as a viscous oil from the main fraction. This crystallizes after standing for a fairly long time (10 weeks) in ethyl acetate/petrol ether. The crystals melt at 62° to 64°.

EXAMPLE 42

N-[N-(p-chlorobenzoyl)-4-(1,1,3,3-tetramethylbutylamino)butyryl]-4-(p-anisidino)butyric acid $R^1$=p-chlorobenzoyl,
$R^2$=—$C(CH_3)_2$—$CH_2$—$C(CH_3)_3$,
$R^3$=p-methoxyphenyl, A=B=—$CH_2$—$CH_2$—$CH_2$—

Analogously to Example 1, by using equivalent quantities, reacting N-(p-chlorobenzoyl)-4-[(1,1,3,3-tetramethylbutyl)amino]butyric acid and methyl 4-(p-anisidino)butyrate and suitable processing, dissolving the evaporation residue in ethanol, adding an ethanolic solution of potassium hydroxide, stirring for 12 hours at room temperature and further processing yields N-[N-(p-chlorobenzoyl-4-(1,1,3,3-tetramethylbutylamino)butyryl]-4-(p-anisidino)butyric acid.

EXAMPLE 43

N-[N-(p-fluorobenzoyl)-4-(1,1,3,3-tetramethylbutylamino)butyryl]-L-proline $R^1$=p-fluorobenzoyl,
$R^2$=—$C(CH_3)_2$—$CH_2$—$C(CH_3)_3$,
A=—$CH_2$—$CH_2$—$CH_2$—, B=—$CH(R^5)$—,
$R^3$+$R^5$=—$CH_2$—$CH_2$—$CH_2$—

Analogously to Example 1, by using equivalent quantities, reacting N-(p-fluorobenzoyl)-4-[(1,1,3,3-tetramethylbutyl)amino]butyric acid and ethyl L-prolinate and suitable processing, dissolving the evaporation residue in ethanol, adding an ethanolic solution of potassium hydroxide, stirring for 12 hours at room temperature and further processing yields N-[N-(p-fluorobenzoyl)-4-(1,1,3,3-tetramethylbutylamino)butyryl]-L-proline.

EXAMPLE 44

N-[N-(p-chlorobenzoyl)-4-(tert.-butylamino)butyryl]-L-serine $R^1$=p-chlorobenzoyl, $R^2$=—$C(CH_3)_3$, $R^3$=—H,
A=—$CH_2$—$CH_2$—$CH_2$—, B=—$CH(R^5)$—,
$R^5$=—$CH_2$—OH Analogously to Example 1, by using equivalent quantites, reacting N-(p-chlorobenzoyl)-4-tert.-butylamino)butyric acid and ethyl L-serinate and suitable processing, dissolving the evaporation residue in ethanol, adding an ethanolic solution of potassium hydroxide, stirring for 12 hours at room temperature and further processing yeilds N-[N-(p-chlorobenzoyl)-4-(tert.-butylamino)butyryl]-L-serine.

EXAMPLE 45

N-[N-(3,4,5-trimethoxybenzoyl)-6-(tert.-butylamino)-hexanoyl]-4-(p-anisidino)butyric acid $R^1$=3,4,5-trimethoxybenzoyl, $R^2$=—$C(CH_3)_3$,
$R^3$=p-methoxyphenyl,
A=—$CH_2$—$CH_2$—$CH_2$—$CH_2$—$CH_2$—,
B=—$CH_2$—$CH_2$—$CH_2$—

Analogously to Example 1, by using equivalent quantities, reacting N-(3,4,5-trimethoxybenzoyl)-6-(tert.-butylamino)caproic acid and ethyl γ-(p-anisidino)butyrate and suitable processing, dissolving the evaporation residue in ethanol, adding an ethanolic solution of potassium hydroxide, stirring for 12 hours at room temperature and further processing yields N-[N-(3,4,5-trimethoxybenzoyl)-6-tert.-butylamino)hexanoyl]-4-(p-anisidino)butyric acid.

EXAMPLE 46

N-[N-(p-chlorobenzoyl)-4-(1,1-dimethylpropylamino)-
butyryl]-4-(2,6-diethylanilino)butyric acid $R^1$=p-chlorobenzoyl, $R^2$=—C(CH$_3$)$_2$—CH$_2$—CH$_3$,
$R^3$=2,6-diethylphenyl, A=B=—CH$_2$—CH$_2$—CH$_2$—

Analogously to Example 1, by using equivalent quantities, reacting N-(p-chlorobenzoyl)-4-[(1,1-dimethylpropyl)amino]butyric acid and ethyl γ-(2,6-diethylanilino)butyrate and suitable processing, dissolving the evaporation residue in ethanol, adding an ethanolic solution of potassium hydroxide, stirring for 12 hours at room temperature and further processing yields N-[N-(p-chlorobenzoyl)-4-(1,1-dimethylpropylamino)-butyryl]-4-(2,6-diethylanilino)butyric acid.

EXAMPLE 47

N-[N-(2,4-dichlorobenzoyl-4-(1,1-dimethyl-
propylamino)butyryl]-4-(p-anisidino)butyric acid $R^1$=2,4-dichlorobenzoyl,
$R^2$=—C(CH$_3$)$_2$—CH$_2$—CH$_3$, $R^3$=p-methoxyphenyl,
A=B=—CH$_2$—CH$_2$—CH$_2$—

Analogously to Example 1, by using equivalent quantities, reacting N-(2,4-dichlorobenzoyl)-4-[(1,1dimethylpropyl)amino]butyric acid and methyl γ-(p-anisidino)butyrate and suitable processing, dissolving the evaporation residue in ethanol, adding an ethanolic solution of potassium hydroxide, stirring for 12 hours at room temperature and further processing yields N-[N-(2,4-dichlorobenzoyl)-4-(1,1-dimethylpropylamino)-butyryl]-4-(p-anisidino)butyric acid.

EXAMPLE 48

N-[N-(n-butyryl)-4-(1,1-dimethylpropylamino)butyryl]-
4-(2-methyl-3-butyn-2-ylamino)butyric acid $R^1$=CH$_3$—CH$_2$—CH$_2$—CO—,
$R^2$=—C(CH$_3$)$_2$—CH$_2$—CH$_3$,
$R^3$=—C(CH$_3$)$_2$—C≡CH,
A=B=—CH$_2$—CH$_2$—CH$_2$—

Analogously to Example 1, by using equivalent quantities, reacting N-(n-butyryl)-4-[(1,1-dimethylpropyl)amino]butyric acid and ethyl 4-[(2-methyl-3-butyn-2-yl)amino]butyrate and suitable processing, dissolving the evaporation residue in ethanol, adding an ethanolic solution of potassium hydroxide, stirring for 12 hours at room temperature and further processing yeilds N-[N-(n-butyryl)4-(1,1-dimethylpropylamino)butyryl]-4-(2-methyl-3-butyn-2-ylamino)butyric acid.

EXAMPLE 49

N-[N-(p-chlorobenzoyl)-4-(1-ethynylcyclohexyl-1-
amino)butyryl]-4-(3-ethyl-1-pentyn-3-ylamino)butyric
acid $R^1$=p-chlorobenzoyl, $R^2$=1-ethylnylcyclohexyl-1,
$R^3$=—C(C$_2$H$_5$)$_2$—C≡CH,
A=B=—CH$_2$—Ch$_2$—CH$_2$—

Analogously to Example 1, by using equivalent quantities, reacting N-(p-chlorobenzoyl-4-[(1-ethynylcyclohexyl-1)-amino]butyric acid and ethyl 4-[(3-ethyl-1-pentyn3-yl)amino]butyrate and suitable processing, dissolving the evaporation residue in ethanol, adding an ethanolic solution of potassium hydroxide, stirring for 12 hours at room temperature and further processing yields N-[p-chlorobenzoyl)-4-(1-ethynylcyclohexyl-1-amino)butyryl]-4-(3-ethyl-1-pentyn-3-ylamino)butyric acid.

EXAMPLE 50

N-{N-(p-chlorobenzoyl)-4-[1-(n-propyl)cyclohexyl-l-
amino]butyryl}-4-(1-ethynylcyclohexyl-1-amino)-
butyric acid $R^1$=p-choorobenzoyl, $R^2$=1-(n-propyl)cyclohexyl-1,
$R^2$=1-ethynylcyclohexyl-1,
A=B=—CH$_2$—CH$_2$—CH$_2$—

Analogously to Example 1, by using equivalent quantities, reacting N-(p-chlorobenzoyl)-4-[(1-propylcyclohexyl-1)-amino]butyric acid and ethyl 4-[(1-ethynylcyclohexyl-1)amino]butyrate and suitable processing, dissolving the evaporation residue in ethanol, adding an ethanolic solution of potassium hydroxide, stirring for 12 hours at room temperature and further processing yields N-{N-(p-chlorobenzoyl)-4-[1-(n-propyl)cyclohexyl-1-amino]butyryl}4-(1-ethynylcyclohexyl-1-amino)butyric acid.

EXAMPLE 51

N-{N-(p-chlorobenzoyl)-4-[1-(n-butyl)cyclopentyl-1-
amino]butyryl}-4-aminobutyric acid $R^1$=p-chlorobenzoyl, $R^2$=1-(n-butyl)cyclopentyl-1,
$R^3$=—H, A=B=—CH$_2$—CH$_2$—CH$_2$—

Analogously to Example 1, by using equivalent quantities, reacting N-(p-chlorobenzoyl)-4-{[1-(n-butyl)cyclopentyl-1]-amino}butyric acid and methyl 4-aminobutyrate and suitable processing, dissolving the evaporation residue in ethanol, adding an ethanolic solution of potassium hydroxide, stirring for 12 hours at room temperature and further processing yields N-}N-(p-chlorobenzoyl-4-[1-(n-butyl)cyclopentyl-1-amino]butyryl}-4-aminobutyric acid.

EXAMPLE 52

N-[N-(p-chlorobenzoyl)-4-(1-adamantylamino)-
butyryl]-3-aminopropionic acid $R^1$=p-chlorobenzoyl, $R^2$=1-adamantyl, $R^3$=—H,
A=—CH$_2$—CH$_2$—CH$_2$—, B=—CH$_2$—CH$_2$—

Analogously to Example 1, by using equivalent quantities, reacting N-(p-chlorobenzoyl)-4-(1-adamantylamino)butyric acid and ethyl 3-aminopropionate and suitable processing, dissolving the evaporation residue in ethanol, adding an ethanolic solution of potassium hydroxide, stirring for 12 hours at room temperature and further processing yields N-[N-(p-chlorobenzoyl)-4-(1-adamantylamino)butyryl]-3-aminopropionic acid.

EXAMPLE 53

N-[N-(p-chlorobenzoyl)-4-(cyclooctylamino)butyryl]-
L-alanine $R^1$=p-chlorobenzoyl, $R^2$=cyclooctyl, $R^3$=—H,
A=—CH$_2$—CH$_2$—CH$_2$—, B=—CH($R^5$)—,
$R^5$=—CH$_3$ Analogously to Example 1, by using equivalent quantities, reacting N-(p-chlorobenzoyl)-4-cyclooctylaminobutyric acid and methyl L-alaninate and suitable processing, dissolving the evaporation residue in ethanol, adding an ethanolic solution of potassium hydroxide, stirring for 12 hours at room temperature and further processing yeilds N-[N-(p-chlorobenzoyl)-4-(cyclooctylamino)butyryl]-L-alanine.

EXAMPLE 54

N-[N-acetyl-4-(benzhydrylamino)butyryl]-6-(benzhydrylamino)caproic acid

R$^1$=CH$_3$—CO—, R$^2$=R$^3$==benzhydryl,
A=—CH$_2$—CH$_2$—CH$_2$—,
B=—CH$_2$—CH$_2$—CH$_2$—CH$_2$—CH$_2$—

Analogously to Example 1, by using equivalent quantities, reacting N-acetyl-4-benzhydrylaminobutyric acid and ethyl 6-benzhydrolyaminocaproate and suitable processing, dissolving the evaporation residue in ethanol, adding an ethanolic solution of potassium hydroxide, stirring for 12 hours at room temperature and further processing yields N-[N-acetyl-4-(benzhydrylamino)butyryl]-6-(benzhydrylamino)caproic acid.

EXAMPLE 55

N-[N-(p-chlorobenzoyl)-4-(benzhydrylamino)butyryl]-5-benzhydrylaminovaleric acid R$^1$=p-chlorobenzoyl, R$^2$=R$^3$=benzhydryl,
A=—CH$_2$—CH$_2$—CH$_2$—,
B=—CH$_2$—CH$_2$—CH$_2$—CH$_2$—

Analogously to Example 1, by using equivalent quantities, reacting N-(p-chlorobenzoyl)-4-benzhydrylaminobutyric acid and ethyl 5-benzhydrylaminovalerate and suitable processing, dissolving the evaporation residue in ethanol, adding an ethanolic solution of potassium hydroxide, stirring for 12 hours at room temperature and further processing yields N-[N-(p-chlorobenzoyl)-4-benzhydrylaminobutyryl]-5-benzhydrylaminovaleric acid.

EXAMPLE 56

N-[N-(p-chlorobenzoyl)-4-(1-phenylethylamino)butyryl]-4-benzylaminobutyric acid

R$^1$=p-chlorobenzoyl, R$^2$=1-phenylethyl, R$^2$=benzyl,
A=B=—CH$_2$—CH$_2$—CH$_2$—

Analogously to Example 1, by using equivalent quantities, reacting N-(p-chlorobenzoyl)-4-(1-phenylethylamino)butyric acid and ethyl 4-benzylaminobutyrate and suitable processing, dissolving the evaporation residue in ethanol, adding an ethanolic solution of potassium hydroxide, stirring for 12 hours at room temperature and further processing yields N-[N-(p-chorobenzoyl)-4-(1-phenylethylamino)butyryl]-4-benzylaminobutyric acid.

EXAMPLE 57

N-[N-(p-chlorobenzoyl)-6-(1-phenylethylamino)hexanoyl]-4-benzylaminobutyric acid R$^1$=p-chlorobenzoyl, R$^2$=1-phenylethyl, R$^3$=benzyl,
A=—CH$_2$—CH$_2$—CH$_2$—CH$_2$—CH$_2$—,
B=—CH$_2$—CH$_2$—CH$_2$—

Analogously to Example 1, by using equivalent quantities, reacting N-(p-chlorobenzoyl)-6-(1-phenylethylamino)caproic acid and ethyl 4-benzylaminobutyrate and suitable processing, dissolving the evaporation residue in ethanol, adding an ethanolic solution of potassium hydroxide, stirring for 12 hours at room temperature and further processing yields N-[N-(p-chlorobenzoyl)-6-(1-phenylethylamino)hexanoyl]-4-benzylaminobutyric acid.

EXAMPLE 58

N-[N-(p-chlorobenzoyl)-4-(homoveratrylamino)butyryl]-4-aminobutyric acid

R$^1$=p-chlorobenzoyl, R$^2$=homoveratryl, R$^3$=—H,
A=B=—CH$_2$—CH$_2$—CH$_2$—

Analogously to Example 1, by using equivalent quantities, reacting N-(p-chlorobenzoyl)-4-homoveratrylaminobutyric acid and methyl 4-aminobutyrate and suitable processing, dissolving the evaporation residue in ethanol, adding an ethanolic solution of potassium hydroxide, stirring for 12 hours at room temperature and further processing yields N-[N-(p-chlorobenzoyl)-4-(homoveratrylamino)butyryl]-4-aminobutyric acid.

EXAMPLE 59

N-[N-(p-chlorobenzoyl)-4-(1,2-diphenylethylamino)butyryl]-3-amino propionic acid R$^1$=p-chlorobenzoyl, R$^2$=1,2-diphenylethyl,
R$^3$=—H, A=—CH$_2$—CH$_2$—CH$_2$—,
B=—CH$_2$—CH$_2$—

Analogously to Example 1, by using equivalent quantities, reacting N-(p-chlorobenzoyl)-4-[(1,2-diphenylethyl)amino]butyric acid and ethyl 3-aminopropionate and suitable processing, dissolving the evaporation residue in ethanol, adding an ethanolic solution of potassium hydroxide, stirring for 12 hours at room temperature and further processing yields N-[N-(p-chlorobenzoyl)-4-(1,2-diphenylethylamino)butyryl]-3-aminopropionic acid.

EXAMPLE 60

N-[N-(p-chlorobenzoyl)-4-aminobutyryl]-L-proline

R$^1$=p-chlorobenzoyl, R$^2$=—H,
A=—CH$_2$—CH$_2$—CH$_2$—, B=—CH(R$^5$)—,
R$^3$+R$^5$=—CH$_2$—CH$_2$—CH$_2$—

Analogously to Example 1, by using equivalent quantities, reacting N-(p-chlorobenzoyl)-4-aminobutyric acid and ethyl L-prolinate and suitable processing, dissolving the evaporation residue in ethanol, adding an ethanolic solution of potassium hydroxide, stirring for 12 hours at room temperature and further processing yields N-[N-(p-chlorobenzoyl)-4-aminobutyryl]-L-proline.

EXAMPLE 61

N-[N-(m-trifluoromethylbenzoyl)-4-(1,1,3,3-tetramethylbutylamino)-butyryl]-3-aminopropionic acid R$^1$=m-trifluoromethylbenzoyl,
R$^2$=—C(CH$_3$)$_2$—CH$_2$—C(CH$_3$)$_3$, R$^3$=—H,
A=—CH$_2$—CH$_2$—CH$_2$—, B=—CH$_2$—CH$_2$—

Analogously to Example 1, by using equivalent quantities, reacting N-(m-trifluoromethylbenzoyl)-4-[(1,1,3,3-tetramethylbutyl)amino]butyric acid and ethyl 3-aminopropionate and suitable processing, dissolving the evaporation residue in ethanol, adding an ethanolic solution of potassium hydroxide, stirring for 12 hours at room temperature and further processing yields N-[N-(m-trifluoromethylbenzoyl)-4-(1,1,3,3-tetramethylbutylamino)butyryl]-3-aminopropionic acid.

EXAMPLE 62

N-[N-crotonoyl-4-(1,1,3,3-tetramethylbutylamino)-butyryl]-6-benzhydrylaminocaproic acid R$^1$=CH$_3$—CH=CH—CO—,
R$^2$=—C(CH$_3$)$_2$—CH$_2$—C(CH$_3$)$_3$, R$^3$=benzhydryl,
A=—CH$_2$—CH$_2$—CH$_2$—,
B=—CH$_2$—CH$_2$—CH$_2$—CH$_2$—CH$_2$—

Analogously to Example 1, by using equivalent quantities, reacting N-crotonoyl-4-[(1,1,3,3-tetramethylbutyl)amino]butyric acid and ethyl 6-benzyhydrylaminohexanoate and suitable processing, dissolving the evaporation residue in ethanol, adding an ethanolic solution of potassium hydroxide, stirring for 12 hours at room temperature and further processing yields N-[N-crotonoyl-4-(1,1,3,3-tetramethylbutylamino)butyryl]-6-benzhydrylaminocaproic acid.

EXAMPLE 63

N-[N-propionyl-4-benzyhydrylaminobutyryl]-5-benzhydrylaminovaleric acid

R$^1$=CH$_3$—CH$_2$—CO—, R$^2$=R$^3$=benzhydryl,
A=—CH$_2$—CH$_2$—CH$_2$—,
B=—CH$_2$—CH$_2$—CH$_2$—CH$_2$—

Analogously to Example 1, by using equivalent quantities, reacting N-propionyl-4-benzhydrylaminobutyric acid and ethyl 5-benzhydrylaminovalerate and suitable processing, dissolving the evaporation residue in ethanol, adding an ethanolic solution of potassium hydroxide, stirring for 12 hours at room temperature and further processing yields N-[N-propionyl-4-benzhydrylaminobutyryl]-5-benzhydrylaminovaleric acid.

EXAMPLE 64

N-[N-(5-chloro-2-methoxybenzoyl)-4-benzhydrylaminobutyryl]-6-benzhydrylaminocaproic acid R$^1$=5-chloro-2-methoxybenzoyl,
R$^2$=R$^3$=benzhydryl, A=—CH$_2$—CH$_2$—CH$_2$—,
B=—CH$_2$—CH$_2$—CH$_2$—CH$_2$—CH$_2$—

Analogously to Example 1, by using equivalent quantities, reacting N-(5-chloro-2-methoxybenzoyl)-4-benzhydrylaminobutyric acid and ethyl 6-benzhydrylaminohexanoate and suitable processing, dissolving the evaporation residue in ethanol, adding an ethanolic solution of potassium hydroxide, stirring for 12 hours at room temperature and further processing yields N-[N-(5-chloro-2-methoxybenzoyl)-4-benzhydrylaminobutyryl]-6-benzyhydrylaminocaproic acid.

EXAMPLE 65

N-(N-acetyl-6-benzhydrylaminohexanoyl)-L-serine

R$^1$=CH$_3$—CO—, R$^2$=benzhydryl, R$^3$=—H,
A=—CH$_2$—CH$_2$—CH$_2$—CH$_2$—CH$_2$—,
B=—CH(R$^5$)—, R$^5$=—CH$_2$OH Analogously to Example 1, by using equivalent quantities, reacting N-acetyl-6-benzhydrylaminocaproic acid and ethyl L-serinate and suitable processing, dissolving the evaporation residue in ethanol, adding an ethanolic solution of potassium hydroxide, stirring for 12 hours at room temperature and further processing yields N-(N-acetyl-6-benzhydrylaminohexanoyl)-L-serine.

EXAMPLE 66

N-[N-isobutyryl-6-benzhydrylaminohexanoyl]-6-benzhydrylaminocaproic acid

R$^1$=CH(CH$_3$)$_2$—CO—, R$^2$=R$^3$=benzhydryl,
A=B=—CH$_2$—CH$_2$—CH$_2$—CH$_2$—CH$_2$—

Analogously to Example 1, by using equivalent quantities, reacting N-isobutyryl-6-benzhydrylaminocaproic acid and ethyl 6-benzhydrylaminocaproate and suitable processing, dissolving the evaporation residue in ethanol, adding an ethanolic solution of potassium hydroxide, stirring for 12 hours at room temperature and further processing yields N-[N-isobutyryl-6-benzhydrylaminohexanoyl]-6-benzhydrylaminocaproic acid.

EXAMPLE 67

N-(N-acetyl-5-benzhydrylaminopentanoyl)-5-benzhydrylaminovaleric acid

R$^1$=CH$_3$—CO—, R$^2$=R$^3$=benzhydryl,
A=B=—CH$_2$—CH$_2$—CH$_2$—CH$_2$—

Analogously to Example 1, by using equivalent quantities, reacting N-acetyl-5-benzhydrylaminovaleric acid and ethyl 5-benzhydrylaminovalerate and suitable processing, dissolving the evaporation residue in ethanol, adding an ethanolic solution of potassium hydroxide, stirring for 12 hours at room temperature and further processing yields N-(N-acetyl-5-benzhydrylaminopentanoyl)-5-benzhydrylaminovaleric acid.

EXAMPLE 68

N-(N-crotonoyl-5-benzhydrylaminopentanoyl)-3-aminopropionic acid

R$^1$=CH$_3$—CH=CH—CO—, R$^2$=benzhydryl,
R$^3$=—H, A=—CH$_2$—CH$_2$—CH$_2$—CH$_2$—,
B=—CH$_2$—CH$_2$—

Analogously to Example 1, by using equivalent quantities, reacting N-crotonoyl-5-benzhydrylaminovaleric acid and ethyl 3-aminopropionate and suitable processing, dissolving the evaporation residue in ethanol, adding an ethanolic solution of potassium hydroxide, stirring for 12 hours at room temperature and further processing yields N-(N-crotonoyl-5-benzhydrylaminopentanoyl)-3-aminopropionic acid.

EXAMPLE 69

N-[N-benzoyl-4-(n-butylamino)butyryl]-6-benzhydrylaminocaproic acid

R$^1$=benzoyl, R$^2$=—CH$_2$—CH$_2$—CH$_2$—CH$_3$,
R$^3$=benzhydryl, A=—CH$_2$—CH$_2$—CH$_2$—,
B=—CH$_2$—CH$_2$—CH$_2$—CH$_2$—CH$_2$—

Analogously to Example 1, by using equivalent quantities, reacting N-benzoyl-4-(n-butylamino)butyric acid and ethyl 6-benzhydrylaminocaproate and suitable processing, dissolving the evaporation residue in ethanol, adding an ethanolic solution of potassium hydroxide, stirring for 12 hours at room temperature and further processing yields N-[N-benzoyl-4-(n-butylamino)butyryl]-6-benzhydrylaminocaproic acid.

EXAMPLE 70

N-[N-(p-chlorobenzoyl)-5-(n-butylamino)pentanoyl]-5-benzhydrylaminovaleric acid $R^1$=p-chlorobenzoyl, $R^2$=—$CH_2$—$CH_2$—$CH_2$—$CH_3$, $R^3$=benzhydryl, A=B=—$CH_2$—$CH_2$—$CH_2$—$CH_2$—

Analogously to Example 1, by using equivalent quantities, reacting N-(p-chlorobenzoyl)-5-(n-butylamino)valeric acid and ethyl 5-benzhydrylaminovalerate and suitable processing, dissolving the evaporation residue in ethanol, adding an ethanolic solution of potassium hydroxide, stirring for 12 hours at room temperature and further processing yields N-[N-(p-chlorobenzoyl)-5-(n-butylamino)pentanoyl]-5-benzhydrylaminovaleric acid.

EXAMPLE 71

N-[N-(p-chlorobenzoyl)-4-benzylaminobutyryl]-4-benzhydrylaminobutyric acid $R^1$=p-chlorobenzoyl, $R^2$=benzyl, $R^3$=benzhydryl, A=B=—$CH_2$—$CH_2$—$CH_2$—

Analogously to Example 1, by using equivalent quantities, reacting N-(p-chlorobenzoyl)-4-benzylaminobutyric acid and ethyl 4-benzhydrylaminobutyrate and suitable processing, dissolving the evaporation residue in ethanol, adding an ethanolic solution of potassium hydroxide, stirring for 12 hours at room temperature and further processing yields N-[N-(p-chlorobenzoyl)-4-benzylaminobutyryl]-4-benzyhydrylaminobutyric acid.

EXAMPLE 72

N-[N-(p-chlorobenzoyl)-5-benzylaminopentanoyl]-6-benzhydrylaminocaproic acid $R^1$=p-chlorobenzoyl, $R^2$=benzyl, $R^3$=benzhydryl, A=—$CH_2$—$CH_2$—$CH_2$—$CH_2$—, B=—$CH_2$—$CH_2$—$CH_2$—$CH_2$—$CH_2$—

Analogously to Example 1, by using equivalent quantities, reacting N-(p-chlorobenzoyl)-5-benzylaminovaleric acid and ethyl 6-benzyhydrylaminocaproate and suitable processing, dissolving the evaporation residue in ethanol, adding an ethanolic solution of potassium hydroxide, stirring for 12 hours at room temperature and further processing yields N-[N-(p-chlorobenzoyl)-5-benzylaminopentanoyl]-6-benzhydrylaminocaproic acid.

EXAMPLE 73

N-[N-(p-chlorobenzoyl)-L-methionyl]-4-benzylaminobutyric acid $R^1$=p-chlorobenzoyl, $R^2$=—H, $R^3$=benzyl, A=—CH($R^4$)—, $R^4$=$CH_3$—S—$CH_2$—$CH_2$—, B=—$CH_2$—$CH_2$—$CH_2$—

Analogously to Example 1, by using equivalent quantities, reacting N-(p-chlorobenzoyl)-L-methionine and ethyl 4-benzylaminobutyrate and suitable processing, dissolving the evaporation residue in ethanol, adding an ethanolic solution of potassium hydroxide, stirring for 12 hours at room temperature and further processing yields N-[N-(p-chlorobenzoyl)-L-methionyl]-4-benzylaminobutyric acid.

EXAMPLE 74

N-[N-(2-furoyl)-2-(p-anisidino)propionyl]-4-(1-phenylethylamino)butyric acid $R^1$=2-furoyl, $R^2$=p-methoxyphenyl, $R^3$=1-phenylethyl, A=—CH($R^4$)—, $R^4$=—$CH_3$, B=—$CH_2$—$CH_2$—$CH_2$—

Analogously to Example 1, by using equivalent quantities, reacting N-(2-furoyl)-2-(p-anisidino)propionic acid and ethyl 4-(1-phenylethylamino)butyrate and suitable processing, dissolving the evaporation residue in ethanol, adding an ethanolic solution of potassium hydroxide, stirring for 12 hours at room temperature and further processing yields N-[N-(2-furoyl)-2-(p-anisidino)propionyl]-4-(1-phenylethylamino)butyric acid.

EXAMPLE 75

Ampoules containing 600 mg of N-[N-acetyl-2-(p-anisidino)acetyl]-4-(p-anisidino)butyric acid; size of batch: 250 kg.

| | |
|---|---|
| N-[N-acetyl-2-(p-anisidino)acetyl]-butyric acid | 15.0 kg |
| Caustic soda solution (10% by wt. NaOH) | approx. 15 kg |
| 1,2-propyleneglycol | 25.0 kg |
| Sodium pyrosulfite | 0.0625 kg |
| Double-distilled water | to make up to 250.0 kg |

25.0 kg of 1,2-propyleneglycol and 150.0 kg of water are placed in a receptacle, 15.0 kg of N-[N-acetyl-2-(p-anisidino)acetyl]butyric acid is added and then caustic soda is added slowly while stirring. When everything has dissolved, the pH is adjusted to 7.5 to 8.0 with caustic soda solution. Sodium pyrosulfite is added and the mixture stirred until everything has dissolved. It is made up to 250 kg with the rest of the water. The solution is packed in 10-ml ampoules and sterilized in an autoclave for 30 minutes at 120°.

EXAMPLE 76

Ampoules containing 600 mg of N-[N-(p-chlorobenzoyl)-4-(2,6-dimethylanilino)butyryl]-4-(p-anisidino)-butyric acid; size of batch: 250 kg.

| | |
|---|---|
| N-[N-(p-chlorobenzoyl)-4-(2,6-dimethylanilino)butyryl]-4-(p-anisidino)butyric acid | 15.0 kg |
| Caustic soda solution (10% by wt. NaOH) | approx. 15 kg |
| 1,2-propyleneglycol | 50.0 kg |
| Double-distilled water | to make up to 250.0 kg |

50.0 kg of 1,2-propyleneglycol and 150.0 kg of water are placed in a receptacle. While stirring, N-[N-(p-chlorobenzoyl)-4-(2,6-dimethylanilino)butyryl]-4-(p-anisidino)butyric acid is added. Then, first of all, 15 kg of caustic soda solution are added, and the mixture is then adjusted to a pH of 7.5 to 8.0. It is made up to 250 kg with water. The solution is packed into 10-ml ampoules and sterilized in an autoclave at 120° for 30 minutes.

EXAMPLE 77

Tablets containing 50 mg of N-[N-(p-chlorobenzoyl)-4-(2,6-dimethylphenyl)butyryl]-4-(p-anisidino)butyric acid

| | |
|---|---|
| N-[N-(p-chlorobenzoyl)-4-(2,6-dimethylphenyl)-butyryl-4-(p-anisidino)butyric acid | 25.0 kg |
| Lactose | 35.0 kg |
| Maize starch | 26.0 kg |
| Polyvinylpyrrolidone (molecular weight approx. 25,000) | 2.5 kg |
| Carboxymethylcellulose | 8.0 kg |
| Talcum | 2.5 kg |
| Magnesium stearate | 1.0 kg |
| | 100.0 kg |

The N-[N-(p-chlorobenzoyl)-4-(2,6-dimethylphenyl)-butyryl]-4-(p-anisidino)butyric acid, the lactose and the maize starch are granulated with polyvinylpyrrolidone in approximately 6 liters of water. The granulate is passed through a sieve with a mesh width of 1.25 mm and, after drying, the carboxymethylcellulose, the talcum and the magnesium stearate are added. The dried granulate is pressed into tablets of 8 mm diameter, 250 mg weight and a hardness of from 5 to 6 kg.

In a similar manner tablets are produced containing N-[N-acetyl-2-(p-anisidino)acetyl]-4-(p-anisidino)-butyric acid or N-[N-(p-chlorobenzoyl-4-(2,6-dimethylanilino)butyryl]-4-aminobutyric acid.

EXAMPLE 78

Tablets containing 100 mg of N-[N-(p-chlorobenzoyl)methionyl]-4-(p-anisidino)butyric acid

| | |
|---|---|
| N-[N-(p-chlorobenzoyl)methionyl]-4-(p-anisidino)butyric acid | 40.0 kg |
| Lactose | 24.0 kg |
| Maize starch | 16.0 kg |
| Polyvinylpyrrolidone (molecular weight 25,000) | 4.0 kg |
| Carboxymethylcellulose | 10.0 kg |
| Talcum | 4.0 kg |
| Magnesium stearate | 2.0 kg |
| | 100.0 kg |

The N-[N-(p-chlorobenzoyl)methionyl]-4-(p-anisidino)butyric acid, the lactose and the maize starch are granulated with the polyvinylpyrrolidone in approximately 5.5 liters of water and, after this, are pressed through a sieve with a mesh width of 1.25 mm. After drying, the carboxymethylcellulose, the talcum and the magnesium stearate are added. On an eccentric tabletting machine the granulate is pressed into tablets of 9 mm diameter, 250 mg weight and a hardness of from 4 to 5 kg.

EXAMPLE 79

Tablets containing 300 mg of N-[N-(p-chlorobenzoyl)-4-(p-anisidino)butyryl]-4-(p-anisidino)butyric acid.

| | |
|---|---|
| N-[N-p-chlorobenzoyl-4-(p-anisidino)-butyryl]-4-(p-anisidino)butyric acid | 60.0 kg |
| Lactose | 12.0 kg |
| Maize starch | 8.0 kg |
| Polyvinylpyrrolidone (molecular wt. approx. 25,000) | 4.0 kg |
| carboxymethylcellulose | 10.0 kg |
| Talcum | 4.0 kg |
| Magnesium stearate | 2.0 kg |
| | 100.0 kg |

N-[N-(p-chlorobenzoyl)-4-(p-anisidino)butyryl]-4-p-anisidino)butyric acid, the lactose and the maize starch are granulated with the polyvinylpyrrolidone in approx. 6 liters of water and pressed through a seive of a mesh width of 1.25 mm. After drying, the carboxymethylcellulose, the talcum and the magnesium stearate are added. On a rotary pelleting machine, the granulate is pressed into tablets of 11 mm diameter, 500 mg weight and a hardness of from 6 to 7 kg.

EXAMPLE 80

10,000 capsules with an active principle content of 50 mg are produced from the following ingredients:

| | |
|---|---|
| N-[N-acetyl-3-(2,6-dimethylanilino)propionyl]-4-(2-ethyl-6-methylanilino)butyric acid | 500 g |
| Microcrystalline cellulose | 495 g |
| Amorphous silica | 5 g |
| | 1000 g |

The active principle in finely-powdered form, the cellulose and the silica are thoroughly mixed and packed into hard gelatin capsules of size 4.

Pharmacology

The N-substituted ω-aminoalkanoyl-ω-aminoalkanoic acids exert a strong influence on the pancreatic secretion of narcotized rats and influence the bile secretion of narcotized rats, in which they are found to be superior to known commercial preparations, such as Piprozoline.

In the tables which follow the compounds investigated are marked by a serial number which is allocated as follows:

| Serial No. | Name of Compound |
|---|---|
| 1 | Piprozoline |
| 2 | N-[N-(p-chlorobenzoyl)-4-(2,6-dimethylanilino)-butyryl]sarcosine |
| 3 | N-[N-(p-chlorobenzoyl)-2-(p-anisidino)acetyl]-sarcosine |
| 4 | N-[N-(p-chlorobenzoyl)-2-(p-anisidino)acetyl]-glycine |
| 5 | N-[N-(p-chlorobenzoyl)-2-(p-anisidino)acetyl]-3-aminopropionic acid |
| 6 | N-[N-(p-chlorobenzoyl)-2-(2,6-dimethylanilino)-acetyl]glycine |
| 7 | N-[N-(p-chlorobenzoyl)-2-(2,6-dimethylanilino)acetyl]-3-aminopropionic acid |
| 8 | N-[N-acetyl-2-(p-anisidino)acetyl]-4-(p-anisidino)butyric acid |
| 9 | N-[N-(p-chlorobenzoyl)-2-(p-anisidino)acetyl]-4-(p-anisidino)butyric acid |
| 10 | N-[N-(p-chlorobenzoyl)-3-(p-anisidino)propionyl]-4-(p-anisidino)butyric acid |
| 11 | N-[N-(p-chlorobenzoyl)-4-(2,6-dimethylanilino)butyryl]-4-(2,6-dimethylanilino)-butyric acid |
| 12 | N-[N-(p-chlorobenzoyl)-4-(p-anisidino)butyryl]-4-(2,6-dimethylanilino)butyric acid |
| 13 | N-[N-(p-chlorobenzoyl)-4-(2,6-dimethylanilino)butyryl]-4-(p-anisidino)butyric acid |
| 14 | N-[N-(p-chlorobenzoyl)-4-(2,6-dimethylanilinobutyryl]-4-aminobutyric acid |
| 15 | N-[N-(3,4,5-trimethoxybenzoyl)-4-(2,6-dimethylanilino)butyryl]-4-aminobutyric acid |
| 16 | N-[N-acetyl-2-(p-anisidino)propionyl]-4-(p-anisidino)butyric acid |
| 17 | N-[N-(2-furoyl)-2-(p-anisidino)propionyl]-4-p-anisidino)butyric acid |
| 18 | N-[N-(p-chlorobenzoyl)-2-(p-anisidino)-propionyl]-4-(p-anisidino)butyric acid |
| 19 | N-[N-(p-trifluoromethylbenzoyl)-2-(p-anisidino)propionyl]-4-(p-anisidino)butyric acid |
| 20 | N-[N-acetyl-3-(2,6-dimethylanilino)-propionyl]-4-(p-anisidino)butyric acid |

-continued

| Serial No. | Name of Compound |
|---|---|
| 21 | N-[N-acetyl-3-(2,6-dimethylanilino)pro-pionyl]-4-(2,6-diethylanilino)butyric acid |
| 22 | N-[N-acetyl-3-(2,6-dimethylanilino)propionyl]-4-(2-ethyl-6-methylanilino)butyric acid |
| 23 | N-[N-(p-chlorobenzoyl)methionyl]-4-(p-anisidino)butyric acid |
| 24 | N-[N-(p-methoxybenzoyl)phenylalanyl]-4-(p-anisidino)butyric acid |
| 25 | N-[N-(p-chlorobenzoyl)-3-(2,6-dimethyl-anilino)propionyl]-4-(p-anisidino)butyric acid |

Table I presents data from investigations of the pancreatic secretion of narcotized rats after intraduodenal application ($ED_{50}$) and the lethal effect on the mouse ($LD_{50}$) after intraperitoneal application of representative compounds (according to the invention) of formula I, as well as the therapeutic quotient (TQ=$LD_{50}$/$ED_{50}$).

TABLE I

Pancreatic Secretion, Toxicity and Therapeutic Quotient

| Serial No. | Toxicity $LD_{50}$ (mg/kg) (mouse, i.p.) | Pancreatic Secretion $ED_{50+}$(mg/kg) (rat, i.d.) | TQ ($LD_{50}$/$ED_{50}$) |
|---|---|---|---|
| 1 | 1070++ | 35 | 31 |
| 2 | 700 | 10 | 70 |
| 3 | >>1000 | 15 | >>67 |
| 4 | >1000 | 15 | >67 |
| 5 | 1300 | 25 | 52 |
| 6 | 400 | ~5 | ~80 |
| 7 | 450 | ≦1 | ≧450 |
| 8 | 1200 | 1 | 1200 |
| 9 | 420 | 3 | 140 |
| 10 | 220 | ~1 | ~220 |
| 11 | 130 | 1 | 130 |
| 12 | 800 | 2 | 400 |
| 13 | 150 | 0.8 | 188 |
| 14 | 400 | 0.4 | 1000 |
| 15 | 800 | ~1 | ~800 |
| 17 | 750 | 5 | 150 |
| 18 | ≦250 | 5 | ≦50 |
| 20 | 600 | 7 | 86 |
| 22 | 430 | 3 | 143 |
| 24 | 300 | 6 | 50 |

+$ED_{50}$ = dose which brings about an increase in the pancreatic secretion (liquid volume; 30-minute fraction) by a maximum of 50%.
++$LD_{50}$ (p.o.) cited from Herrmann et al., Arzneimittel-Forschung, 27 (1977) 467.

Table II presents data from investigations of the bile secretion (choleresis) of narcotized rats after intraduodenal application ($ED_{50}$) and the lethal effect on the mouse ($LD_{50}$) after intraperitoneal application of representative compounds according to the invention, as well as the therapeutic quotient (TQ=$LD_{50}$$ED_{50}$).

TABLE II

Bile Secretion, Toxicity and Therapeutic Quotient

| Serial No. | Toxicity $LD_{50}$ (mg/kg) (mouse i.p.) | Bile Secretion $ED_{50+++}$(mg/kg) (rat, i.d.) | TQ ($LD_{50}$/$ED_{50}$) |
|---|---|---|---|
| 1 | 1070++ | 40 | 27 |
| 7 | 450 | 10 | 45 |
| 11 | 130 | 3 | 43 |
| 12 | 800 | 14 | 57 |
| 16 | 600 | 10 | 60 |
| 17 | 750 | 11 | 68 |
| 18 | ≦250 | 7 | ≦36 |
| 19 | 130 | ~1 | ~130 |
| 20 | 600 | 7 | 86 |
| 21 | 280 | ~1 | ~280 |
| 22 | 430 | 1.3 | 331 |
| 23 | 700 | 2.5 | 280 |
| 24 | 300 | 6 | 50 |
| 25 | 60 | ~1 | ~60 |

+++$ED_{50}$ = the dose which brings about an increase in the bile secretion (liquid volume; 30-min. fraction) by a maximum of 50%.
++$LD_{50}$ (p.o.), cited from Herrmann et al., Arzneimittel-Forschung, 27 (1977) 467.

The determination of the pharmacological properties was carried out by the following methods:

Influence on the Pancreatic and Bile Secretion of the Narcotized Rat Carrying out the Test Male Sprague-Dawley rats (250 to 300 g body weight) are narcotized with 1.2 g/kg urethane i.m. Then the abdominal cavity is opened medially, the Ductus choledochus ligatured shortly above its entry into the duodenum and also near the liver joint, and both sections are catheterized towards the liver.

As in the case of the rat all pancreatic ducts lead into the center section of the Ductus choledochus; it is thus possible in this way to derive separately the pancreatic secreta from the distal (ligatured) section and the bile from the proximal section of the Ductus choledochus.

The separated quantities of pancreatic juice and bile juice are measured at intervals of 30 minutes during the period from before 2 hours to 3 hours after the intraduodenal (V. jugularis externa) administration of the compounds to be tested (volume of liquid administered 5 ml/kg).

The body temperature of the animals is maintained at from 36° to 38° C. by means of electric blankets and radiation; the monitoring of the temperature is carried out rectally.

Assessment:

The liquid volumes of the 30-minute fractions after the administration of the product are related in each case to the quantity of bile or pancreatic juice secreted prior to the application of the substance (=100%, mean of the two last measurements). The maximum percentage increase of the pancreatic or bile secretion is plotted against the dose and, from this, the $ED_{50}$ is determined by interpolation.

Determination of the Toxicity

The toxicity tests are carried out on female NMRI mice (body weight: 22 to 26 g). The animals (5 animals per dose) are given food and water ad lib. Different dosages of the substances are administered intraperitoneally. The duration of observation is 14 days. The $LD_{50}$, i.e. the dose at which 50% of the animals die, is determined graphically from the dose/effect curve.

The preceding disclosure adequately apprises those of ordinary skill in the relevant art:

a. what the subject invention is, including its metes and bounds;

b. how to make and use the novel compounds from known chemicals or from chemicals which are synthesized by established and recognized procedures from available starting materials;

c. how to prepare the novel compositions; and d. how to use the compounds and the compositions, and makes it clear that changes in structure and composition components are readily made without departing from the spirit or scope of the instant teachings.

What is claimed is:

1. A compound which, in free-acid form, is a pharmacologically-acceptable ω-aminoalkanoyl-ω-aminoalkanoic acid of the formula $$R^1-N-A-CO-N-B-COOH$$
$$\phantom{R^1-N-}|\phantom{A-CO-}|$$
$$\phantom{R^1-N-}R^2\phantom{-CO-}R^3$$

wherein $R^1$ is a member selected from the group consisting of hydrocarbyl-aliphatic carbonyl having from 2 to 8 carbon atoms, hydrocarbyl-alicyclic carbonyl from 3 to 10 ring carbon atoms, optionally-substituted benzoyl, 2-furoyl, 3-furoyl, 2-thenoyl, 3-thenoyl, nicotinoyl, isonicotinoyl, picolinoyl, 2-pyrrolecarbonyl and 3-pyrrolecarbonyl;

$R^2$ is —H, cycloalkyl with from 5 to 8 ring carbon atoms, 1-(hydrocarbyl-aliphatic with up to 5 carbon atoms)-substituted cycloalkyl with from 5 to 8 ring carbon atoms, adamantyl, phenyl, substituted phenyl, substitued lower alkyl, branched-chain lower alkyl or (when $R^3$ is other than straight-chain lower alkyl) straight-chain lower alkyl;

$R^3$ is substituted lower alkyl, branched-chain lower alkyl, straight-chain lower alkyl, phenyl, substituted phenyl, cycloalkyl with from 5 to 8 ring carbon atoms, 1-(hydrocarbyl-aliphatic with up to 5 carbon atoms)-substituted cycloalkyl with from 5 to 8 ring carbon atoms, adamantyl, or (when $R^2$ is other than —H) —H, or (jointly with $R^5$) trimethylene;

$R^4$ is methyl, benzyl, hydroxymethyl, 2-hydroxyethyl, methylmercaptomethyl or 2-methylmercaptoethyl;

$R^5$ is, independently, one of the meanings ascribed to $R^4$ or, together with $R^3$, trimethylene;

A is —$(CH_2)_m$— or —$CH(R^4)$—;

B is —$(CH_2)_n$— or —$CH(R^5)$—; and each of m and n is, independently, a positive whole number of at most 5;

each substituted lower alkyl is a radical of the formula

—$C(R^9)(R^{10})(R^{11})$;

each $R^9$ is, independently, —H, alkyl with from 1 to 5 carbon atoms, alkenyl with from 2 to 5 carbon atoms or alkynyl with from 2 to 5 carbon atoms;

each $R^{10}$ is, independently, —H, alkyl with from 1 to 5 carbon atoms, cycloalkyl with from 3 to 8 ring carbon atoms or optionally-substituted phenyl;

each $R^{11}$ is, independently, alkyl with from 1 to 5 carbon atoms, cycloalkyl with from 3 to 8 ring carbon atoms, cycloalkylalkyl with from 3 to 8 ring carbon atoms and from 1 to 3 carbon atoms in the alkyl, optionally-substituted phenyl or (optionally-substituted phenyl)-alkyl with from 1 to 3 carbon atoms in the alkyl; and any substituent of substituted phenyl or of substituted benzoyl is a member selected from the group consisting of halo, alkyl, having up to 8 carbon atoms, hydroxy, alkoxy having up to 8 carbon atoms, alkylmercapto having up to 8 carbon atoms, carboxylic acid acyloxy, organic carbonic acid acyloxy, optionally-substituted amino wherein any substituent is alkanoyl having from 2 to 5 carbon atoms or lower alkyl, nitro, trifluoromethyl, trifluoromethoxy and trifluoromethylmercapto.

2. An ω-(substituted amino)alkanoly-ω-aminoalkanoic acid according to claim 1.

3. A compound according to claim 1 in the form of a salt with a base.

4. A pharmacologically-acceptable compound according to claim 3.

5. A compound according to claim 1 wherein $R^1$ is hydrocarbyl-aliphatic carbonyl, hydrocarbyl-alicyclic carbonyl, optionally-substituted benzoyl, 2-furoyl, 2-thenoyl or nicotinoyl.

6. A compound according to claim 1 wherein $R^1$ is hydrocarbyl-aliphatic carbonyl.

7. A compound according to claim 1 wherein $R^1$ is hydrocarbyl-alicyclic carbonyl.

8. A compound according to claim 1 wherein $R^1$ is phenyl carbonyl or substituted-phenyl carbonyl.

9. A compound according to claim 1 wherein $R^1$ is 2- or 3-furoyl.

10. A compound according to claim 1 wherein $R^1$ is 2- or 3-thenoyl.

11. A compound according to claim 1 wherein $R^1$ is nicotinoyl or isonicotinoyl.

12. A compound according to claim 1 wherein $R^1$ is picolinoyl.

13. A compound according to claim 1 wherein $R^1$ is 2- or 3-pyrrolecarbonyl.

14. A compound according to claim 1 which, in free-acid form, is of one of the formulae:

$$R^1-N-(CH_2)_m-CO-N-(CH_2)_n-COOH \quad (I\text{-}A)$$
$$\phantom{R^1-N-}|\phantom{(CH_2)_m-CO-}|$$
$$\phantom{R^1-N-}R^2\phantom{(CH_2)_m-CO-}R^3$$

$$R^1-N-(CH_2)_m-CO-N-\overset{*}{C}H-COOH \quad (I\text{-}B)$$
$$\phantom{R^1-N-}|\phantom{(CH_2)_m-CO-}|\phantom{\overset{*}{C}}|$$
$$\phantom{R^1-N-}R^2\phantom{(CH_2)_m-CO-}R^3\; R^5$$

$$R^1-N-\overset{*}{C}H-CO-N-(CH_2)_n-COOH \quad (I\text{-}C)$$
$$\phantom{R^1-N-}|\phantom{\overset{*}{C}}|\phantom{-CO-}|$$
$$\phantom{R^1-N-}R^2\; R^4\phantom{-CO-}R^3$$

$$R^1-N-\overset{*}{C}H-CO-N-\overset{*}{C}H-COOH \quad (I\text{-}D)$$
$$\phantom{R^1-N-}|\phantom{\overset{*}{C}}|\phantom{-CO-}|\phantom{\overset{*}{C}}|$$
$$\phantom{R^1-N-}R^2\; R^4\phantom{-CO-}R^3\; R^5$$

$$R^1-N-(CH_2)_m-CO-N———CH-COOH \quad (I\text{-}E)$$
$$\phantom{R^1-N-}|\phantom{(CH_2)_m-CO-N———CH}$$
$$\phantom{R^1-N-}R^2\phantom{(CH_2)_m-CO}\smile$$

$$R^1-N-\overset{*}{C}H-CO-N———CH-COOH \quad (I\text{-}F)$$
$$\phantom{R^1-N-}|\phantom{\overset{*}{C}}|\phantom{-CO-N———CH}$$
$$\phantom{R^1-N-}R^2\; R^4\phantom{-CO}\smile$$

wherein $R^2$ is —H, cycloalkyl with from 5 to 8 ring carbon atoms, 1-(hydrocarbyl-aliphatic with up to 5 carbon atoms)-substituted cycloalkyl with from 5 to 8 ring carbon atoms, adamantyl, optionally-substituted phenyl or —$C(R^9)(R^{10})$—$(R^{11})$, with the proviso that $R^2$ is not —H when $R^3$ is —H and that $R^2$ is not straight-chain lower alkyl when $R^3$ is straight-chain lower alkyl;

$R^3$ is —H, cycloalkyl with from 5 to 8 ring carbon atoms, 1-(hydrocarbyl-aliphatic with up to 5 carbon atoms)-substituted cycloalkyl with from 5 to 8 ring carbon atoms, adamantyl, optionally-substituted phenyl, methyl or —$C(R^9)(R^{10})(R^{11})$;

each of $R^4$ and $R^5$ is, independently, methyl, benzyl, hydroxymethyl, 2-hydroxyethyl, methylmercaptomethyl or 2-methylmercaptoethyl;

each $R^9$ is, independently, —H, alkyl with from 1 to 5 carbon atoms, alkenyl with from 2 to 5 carbon atoms or alkynyl with from 2 to 5 carbon atoms;

each $R^{10}$ is, independently, —H, alkyl with from 1 to 5 carbon atoms, cycloalkyl with from 3 to 8 ring carbon atoms or optionally-substituted phenyl;

each $R^{11}$ is, independently, alkyl with from 1 to 5 carbon atoms, cycloalkyl with from 3 to 8 ring carbon atoms, cycloalkylalkyl with from 3 to 8 ring carbon atoms and from 1 to 3 carbon atoms in the alkyl, optionally-substituted phenyl or (optionally-substituted phenyl)-alkyl with from 1 to 3 carbon atoms in the alkyl; and each of m and n is, independently, a positive whole number of at most 5.

15. A compound according to claim 14 wherein the phenyl ring of optionally-substituted benzoyl and each optionally-substituted phenyl is, independently, a radical of the formula

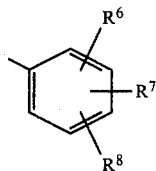

(Ph), wherein each of $R^6$, $R^7$ and $R^8$ is, independently, a member selected from the group consisting of —H, halo, lower alkyl, hydroxy, lower alkoxy, lower alkylmercapto, —O—$R^1$, optionally-substituted amino wherein any substituent is alkanoyl having from 2 to 5 carbon atoms or lower alkyl, nitro, trifluoromethyl, trifluoromethoxy or trifluoromethylmercapto.

16. A compound according to claim 15 which, in free-acid form, is of formula I-A.

17. A compound according to claim 15 which, in free-acid form, is of formula I-B.

18. A compound according to claim 15 which, in free-acid form, is of formula I-C.

19. A compound according to claim 15 which, in free-acid form, is of formula I-D.

20. A compound according to claim 15 which, in free-acid form, is of formula I-E.

21. A compound according to claim 15 which, in free-acid form, is of formula I-F.

22. A compound according to claim 15 wherein $R^1$ is hydrocarbyl-aliphatic carbonyl and $OR^1$ in the definition of each of $R^6$, $R^7$ and $R^8$ is alkanoyloxy having from 2 to 5 carbon atoms.

23. A compound according to claim 15 wherein $R^1$ is hydrocarbyl-alicyclic carbonyl and $OR^1$ in the definition of each of $R^6$, $R^7$ and $R^8$ is alkanoyloxy having from 2 to 5 carbon atoms.

24. A compound according to claim 15 wherein $R^1$ is phenyl carbonyl or substituted-phenyl carbonyl and $OR^1$ in the definition of each of $R^6$, $R^7$ and $R^8$ is alkanoyloxy having from 2 to 5 carbon atoms.

25. A compound according to claim 15 wherein $R^1$ is 2- or 3-furoyl and $OR^1$ in the definition of each of $R^6$, $R^7$ and $R^8$ is alkanoyloxy having from 2 to 5 carbon atoms.

26. A compound according to claim 15 wherein $R^1$ is 2- or 3-thenoyl and $OR^1$ in the definition of each of $R^6$, $R^7$ and $R^8$ is alkanoyloxy having from 2 to 5 carbon atoms.

27. A compound according to claim 15 wherein $R^1$ is nicotinoyl or isonicotinoyl and $OR^1$ in the definition of each of $R^6$, $R^7$ and $R^8$ is alkanoyloxy having from 2 to 5 carbon atoms.

28. A compound according to claim 15 wherein $R^1$ is picolinoyl and $OR^1$ in the definition of each of $R^6$, $R^7$ and $R^8$ is alkanoyloxy having from 2 to 5 carbon atoms.

29. A compound according to claim 15 wherein $R^1$ is 2- or 3-pyrrolecarbonyl and $OR^1$ in the definition of each of $R^6$, $R^7$ and $R^8$ is alkanoyloxy having from 2 to 5 carbon atoms.

30. A compound according to claim 1 wherein $R^1$ is alkanoyl having from 2 to 5 carbon atoms, alkenoyl having from 2 to 5 carbon atoms, 2-furoyl or —CO—Ph;

$R^2$ is —H, cycloalkyl with from 5 to 8 ring carbon atoms, 1-(alkyl with from 1 to 4 carbon atoms or ethynyl)-substituted cycloalkyl with from 5 to 8 ring carbon atoms, adamantyl-(1), —Ph, or —C($R^9$) ($R^{10}$) ($R^{11}$), with the proviso that $R^2$ is not —H when $R^3$ is —H and that $R^2$ is not straight-chain lower alkyl when $R^3$ is straight-chain lower alkyl;

$R^3$ is —H, cycloalkyl with from 5 to 8 ring carbon atoms, 1-(alkyl with from 1 to 4 carbon atoms or ethynyl)-substituted cycloalkyl with from 5 to 8 ring carbon atoms, —Ph, adamantyl-(1), methyl or —C($R^9$) ($R^{10}$) ($R^{11}$);

A is —(CH$_2$)$_m$—;

B is —(CH$_2$)$_n$—;

each of m and n is, independently, a positive whole number of at most 5;

each Ph is, independently, a radical of the formula

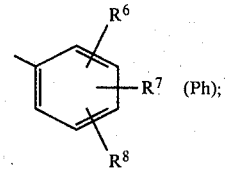

(Ph);

each $R^6$, each $R^7$ and each $R^8$ is, independently, a member selected from the group consisting of —H, —OH, halo, alkyl with from 1 to 4 carbon atoms, alkoxy with from 1 to 4 carbon atoms, alkanoyloxy with from 2 to 5 carbon atoms, amino, nitro and trifluoromethyl;

$R^9$ is —H, alkyl with from 1 to 4 carbon atoms or ethynyl;

$R^{10}$ is —H, alkyl with from 1 to 4 carbon atoms or —Ph; and $R^{11}$ is alkyl with from 1 to 5 carbon atoms, —Ph or —CH$_2$—Ph.

31. A compound according to claim 30 in which $R^1$ is alkanoyl with from 2 to 5 carbon atoms or —CO—Ph; $R^2$ is —H, —($R^9$) ($R^{10}$) ($R^{11}$) or —Ph; $R^3$ is —H or —C($R^9$) ($R^{10}$) ($R^{11}$); A is —(CH$_2$)$_m$—; B is —(CH$_{2n}$)-; each of m and n is, independently, a positive whole number of from 1 to 5; each $R^6$ and each $R^7$ is, independently, —H, halo, methyl, methoxy, amino, nitro or trifluoromethyl; $R^8$ is —H; $R^9$ is —H or methyl; $R^{10}$ is —H or —Ph, or, together with $R^{11}$, pentamethylene or heptamethylene; $R^{11}$ is —Ph or —CH$_2$—Ph, or, together with $R^{10}$, pentamethylene or heptamethylene.

32. A compound according to claim 31 in which $R^1$ is alkanoyl with from 2 to 5 carbon atoms or —CO—Ph; $R^2$ is —H or —Ph; $R^3$ is —H or —C($R^9$) ($R^{10}$) ($R^{11}$); A is trimethylene; B is —(CH$_2$)$_n$—; n is a positive whole number from 3 to 5; each Ph is, independently, a radical of the formula

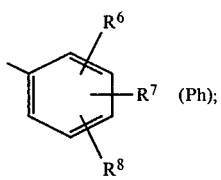

$R^6$ is —H, chloro, methoxy or trifluoromethyl; $R^7$ is —H, chloro or methoxy; $R^8$ is —H; $R^9$ is —H; $R^{10}$ is Ph; $R^{11}$ is —Ph or —CH$_2$—Ph.

33. A compound according to claim 30 wherein
$R^1$ is alkanoyl with from 2 to 5 carbon atoms, alkenoyl with from 2 to 5 carbon atoms, 2-furoyl or —CO—Ph;
$R^2$ is —H or —Ph;
$R^3$ is —H or —Ph;
A is —(CH$_2$)$_m$—;
B is —(CH$_2$)$_n$—;
each of m and n is, independently, a positive whole number of at most 5;
each $R^6$, each $R^7$ and each $R^8$ is, independently, —H, halo, alkyl with from 1 to 4 carbon atoms, alkoxy with from 1 to 4 carbon atoms, —OH, alkanoyloxy with from 2 to 5 carbon atoms, amino, nitro or trifluoromethyl.

34. A compound according to claim 33 in which $R^1$ is alkanoyl with from 2 to 5 carbon atoms or —CO—Ph; $R^2$ is —H or —Ph; $R^3$ is —H or —Ph; A is —(CH$_2$)$_m$—; B is —(CH$_2$)$_n$—; m is a positive whole number of at most 3; n is a positive whole number from 3 to 5, inclusive; each $R^6$ is —H; each $R^7$ and each $R^8$ is, independently, —H, halo, methyl, ethyl, methoxy, amino, nitro or trifluoromethyl.

35. A compound according to claim 34 in which $R^1$ is alkanoyl with from 2 to 5 carbon atoms or —CO—Ph; $R^2$ is —Ph; $R^3$ is —H or —Ph; A is —(CH$_2$)$_m$—; B is trimethylene; m is a positive whole number of at most 3; each $R^6$ is —H; each $R^7$ is chloro, methyl, ethyl or methoxy; and each $R^8$ is —H, methyl or ethyl.

36. A compound according to claim 34 in which $R^1$ is alkanoyl with from 2 to 5 carbon atoms or —CO—Ph; $R^2$ is —Ph; $R^3$ is —H or —Ph; A is —(CH$_2$)$_m$—; B is trimethylene; m is a positive whole number of at most 3; $R^6$ is —H; $R^7$ is —H, chloro, methyl, methoxy or trifluoromethyl; $R^8$ is —H, chloro, ethyl or methoxy.

37. A compound according to claim 1 wherein
$R^1$ is alkanoyl with from 2 to 5 carbon atoms, alkenoyl with from 2 to 5 carbon atoms, 2-furoyl or —CO—Ph;
$R^2$ is —H or —Ph;
$R^3$ is —H (but not when $R^2$ is —H), cycloalkyl with from 5 to 8 ring carbon atoms, 1-(alkyl with from 1 to 3 carbon atoms or ethynyl)-substituted cycloalkyl with from 5 to 8 ring carbon atoms, —C($R^9$)($R^{10}$)($R^{11}$), Ph or, jointly with $R^5$, trimethylene; Ph is a radical of the formula

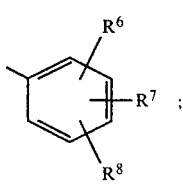

A is —(CH$_2$)$_m$— or —CH($R^4$)—;

B is —(CH$_2$)$_n$— or —CH($R^5$)—, with the proviso that A and B do not simultaneously represent straight-chain alkylene groups;
each of m and n is, independently, a positive whole number of at most 5;
$R^4$ is methyl, benzyl, hydroxymethyl or 2-methylmercaptoethyl;
$R^5$ is one of the meanings of $R^4$ or, together with $R^3$, trimethylene;
each $R^6$, each $R^7$ and each $R^8$ is, independently, —H, —OH, halo, alkyl with from 1 to 4 carbon atoms, alkoxy with from 1 to 4 carbon atoms, alkanoyloxy with from 2 to 5 carbon atoms, amino, nitro or trifluoromethyl;
$R^9$ is —H, alkyl with from 1 to 3 carbon atoms or ethynyl;
$R^{10}$ is —H, alkyl with from 1 to 3 carbon atoms, cycloalkyl with from 3 to 8 ring carbon atoms or —Ph or together with $R^{11}$, an alkylene group with from 4 to 7 carbon atoms; and
$R^{11}$ is alkyl with from 1 to 3 carbon atoms, cycloalkyl with from 3 to 8 ring carbon atoms, —Ph or —CH$_2$—Ph, or together with $R^{10}$, an alkylene group with from 4 to 7 carbon atoms.

38. A compound according to claim 37 in which $R^1$ is alkanoyl with from 2 to 5 carbon atoms or—CO—Ph; $R^2$ is —H or —Ph; $R^3$ is —Ph or, together with $R^5$, trimethylene; A is —(CH$_2$)$_m$— or —CH($R^4$)—; B is a —(CH$_2$)$_n$— or —CH($R^5$)—; either A is —(CH$_2$)$_m$— or B is —(CH$_2$)$_n$—; each of m and n is, independently, a positive whole number of from 3 to 5, inclusive; $R^4$ is methyl, benzyl, hydroxymethyl or 2-methylmercaptoethyl; $R^5$ is one of the meanings ascribed to $R^4$ or, jointly with $R^3$, trimethylene; $R^6$ is —H; each $R^7$ and each $R^8$ is, independently, —H, halo, methyl, methoxy, nitro, amino or trifluoromethyl.

39. A compound according to claim 38 in which $R^1$ is alkanoyl with from 2 to 5 carbon atoms or —CO—Ph; $R^2$ is —H or—Ph; $R^3$ is —Ph; A is —CH($R^4$)—; B is trimethylene; $R^4$ is methyl, benzyl or 2-methylmercaptoethyl, $R^6$ is —H; $R^7$ is —H, chloro, methoxy, methyl or trifluoromethyl; $R^7$ is —H, chloro, methyl or methoxy.

40. A compound according to claim 1 which is N-[N-acetyl-2-(p-anisidino)acetyl]-4-(p-anisidino)butyric acid or a pharmacologically-compatible salt thereof with an inorganic or organic base.

41. A compound according to claim 1 which is N-[N-(p-chlorobenzoyl)-4-(2,6-dimethylanilino)butyryl]-4-(p-anisidino)butyric acid or a pharmacologically-compatible salt thereof with an inorganic or organic base.

42. A compound according to claim 1 which is N-[N-(p-chlorobenzoyl)-4-(2,6-dimethylanilino)butyryl]-4-aminobutyric acid or a pharmacologically-compatible salt thereof with an inorganic or organic base.

43. A compound according to claim 1 which is N-[N-(3,4,5-trimethoxybenzoyl)-4-(2,6-dimethylanilino)-butyryl]-4-aminobutyric acid or a pharmacologically-compatible salt thereof with an inorganic or organic base.

44. A compound according to claim 1 which is N-[N-acetyl-3-(2,6-dimethylanilino)propionyl]-4-(2-ethyl-6-methylanilino)butyric acid or a pharmacologically-compatible salt thereof with an inorganic or organic base.

45. A compound according to claim 1 which is N-[N-(p-chlorobenzoyl)-methionyl]-4-(p-anisidino)butyric acid or a pharmacologically-compatible salt thereof with an inorganic or organic base.

46. The compound according to claim 35 which is N-[N-(p-chlorobenzoyl)-4-(p-anisidino)butyryl]-4-(2,6-dimethylanilino-butyric acid.

47. A pharmaceutical composition comprising active principle and excipient or carrier therefor, the active principle comprising from 0.5 to 1000 milligrams (per unit dose) of a pharmacologically-acceptable compound according to claim 1.

48. A process for treating or for prophylaxis of a disease which is attributable to stomach or intestine disorders or to reduced performance of the pancreas, gall bladder and/or liver which comprises administering to a mammal afflicted with or subject to such disorder an effective amount of a pharmacologically-acceptable compound according to claim 1.

49. A process according to claim 48 which comprises administering to the mammal with a diseased pancreas an effective amount of the pharmacologically-acceptable compound.

50. A process according to claim 48 which comprises administering to the mammal with a diseased liver an effective amount of the pharmacologically-acceptable compound.

51. A process according to claim 48 which comprises administering to the mammal with diseased bile an effective amount of the pharmacologically-acceptable compound.

52. A process according to claim 48 which comprises administering to the mammal afflicted with diseased stomach an effective amount of the pharmacologically-acceptable compound.

53. A process according to claim 48 which comprises administering to the mammal afflicted with diseased intestine an effective amount of the pharmacologically-acceptable compound.

* * * * *